United States Patent
Yamamoto et al.

(10) Patent No.: US 7,195,586 B2
(45) Date of Patent: Mar. 27, 2007

(54) APPARATUS AND METHOD FOR FOLDING AND TUCKING DISPOSABLE DIAPERS IN THEIR CROTCH REGIONS

(75) Inventors: Hiroki Yamamoto, Kagawa-ken (JP); Akihisa Shiomi, Kagawa-ken (JP); Akihide Ninomiya, Kagawa-ken (JP); Takanori Yano, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 101 days.

(21) Appl. No.: 11/056,271

(22) Filed: Feb. 14, 2005

(65) Prior Publication Data

US 2005/0148946 A1    Jul. 7, 2005

Related U.S. Application Data

(63) Continuation of application No. PCT/JP03/10790, filed on Aug. 26, 2003.

(30) Foreign Application Priority Data

Aug. 28, 2002  (JP)  ............................. 2002-248447
Jul. 23, 2003   (JP)  ............................. 2003-200578

(51) Int. Cl.
    *B31F 1/08* (2006.01)
(52) U.S. Cl. .................. 493/429; 493/431; 156/164; 156/161
(58) Field of Classification Search ............... 493/429, 493/431, 437, 446; 156/164, 161, 204, 229
See application file for complete search history.

(56) References Cited

U.S. PATENT DOCUMENTS

| | | | | |
|---|---|---|---|---|
| 3,552,736 A | * | 1/1971 | Frick et al. ................. | 493/331 |
| 4,563,185 A | * | 1/1986 | Reiter ..................... | 604/385.3 |
| 4,938,821 A | * | 7/1990 | Soderlund et al. ........... | 156/85 |
| 5,069,678 A | * | 12/1991 | Yamamoto et al. .... | 604/385.21 |
| 5,429,694 A | * | 7/1995 | Herrmann ................... | 156/164 |
| 5,626,711 A | * | 5/1997 | Herrmann ................... | 156/496 |

(Continued)

FOREIGN PATENT DOCUMENTS

EP    1 177 782 A1    2/2002

(Continued)

*Primary Examiner*—Sameh H. Tawfik
(74) *Attorney, Agent, or Firm*—Lowe Hauptman & Berner LLP

(57) ABSTRACT

An apparatus includes a first rotary disc, a plurality of folding plates arranged at regular intervals along a peripheral zone of the first rotary disc, a plurality of positive motion cams arranged at regular intervals along the peripheral zone of the first rotary disc so as to be interposed between the first rotary disc and the folding plates, a second rotary disc located on the opposite side of the first rotary disc and a plurality of auxiliary plates arranged at regular intervals along a peripheral zone of the second rotary disc. One of the folding plates and one of the auxiliary plates synchronously move into the inside of a contiguous diaper structure and simultaneously the guide arms move into a clearance between the guide blades so that the opposite side edge zones of the crotch region may be held between the guide arms and the guide blades and thereby the crotch region may be tucked into the contiguous diaper structure.

7 Claims, 13 Drawing Sheets

U.S. PATENT DOCUMENTS

| | | | | |
|---|---|---|---|---|
| RE37,154 E | * | 5/2001 | Nomura et al. | 156/164 |
| 6,620,276 B1 | * | 9/2003 | Kuntze et al. | 156/164 |
| 6,730,188 B2 | * | 5/2004 | Sanders | 156/256 |
| 6,913,664 B2 | * | 7/2005 | Umebayashi et al. | 156/64 |
| 6,926,654 B2 | * | 8/2005 | Yamamoto et al. | 493/254 |
| 7,013,941 B2 | * | 3/2006 | Schneider et al. | 156/443 |

FOREIGN PATENT DOCUMENTS

| | | |
|---|---|---|
| JP | 05-031135 A | 2/1993 |
| JP | 05-031136 A | 2/1993 |
| JP | 05-042180 A | 2/1993 |
| JP | 3021190 U | 11/1995 |
| JP | 09-131364 A | 5/1997 |

* cited by examiner

APPARATUS AND METHOD FOR FOLDING AND TUCKING DISPOSABLE DIAPERS IN THEIR CROTCH REGIONS

BACKGROUND OF THE INVENTION

The present invention relates to an apparatus and a method for folding and tucking disposable diapers in their crotch regions inward as a contiguous diaper structure is fed in a machine direction.

Various processes for making pull-on diapers are well known, including a typical example as will be described below.

This typical process comprises the steps of forming a continuous laminate including a liquid-pervious continuous first web and a liquid-impervious continuous second web which run in a longitudinal direction of these webs and are overlaid each other and liquid-absorbent cores which are interposed between the webs so as to be aligned in the longitudinal direction of the webs at regular intervals, folding back the laminate along a longitudinal center line of the webs with the second web inside, joining the laminates overlaid each other in a heat-sealing line extending in the transverse direction of the webs between each pair of the liquid-absorbent cores adjacent to each other, cutting out the laminate along respective first cutting lines each being convex toward the longitudinal direction to form leg-holes and finally cutting the laminate along second cutting lines each extending in the transverse direction of the webs between each pair of the heat-sealing lines adjacent to each other to obtain a plurality of individual pull-on diapers. The pull-on diaper made by such a conventional process is composed of a front waist region, a rear waist region and a crotch region so to define a waist-hole and a pair of leg-holes.

The process for making a pull-on diaper is disclosed, for example, in Japanese Patent Application Publication Nos. 1993-31135A, 1993-31136A and 1993-42180A.

In the case of the diaper made by the process as has exemplarily been described above, the leg-holes open laterally with respect to the waist-hole which opens in the vertical direction of the diaper as viewed from above with the waist-hole broadened with the hands. In other words, the waist-hole is out of linear alignment with the leg-holes and the crotch region lies immediately below the waist-hole. With such diaper, the wearer's toes or heels come up against transversely opposite side edges of the crotch region as the wearer's legs are let through the waist-hole and the leg-holes when the diaper is put on the wearer's body. In consequence, a much time may be taken to put the diaper on the wearer's body.

From the other viewpoint also, such diaper of the prior art is inconvenient due to the minimum width of the crotch region usually being larger than that of the wearer's crotch. Specifically, the crotch region of the diaper too bulky to be properly received by the wearer's crotch region creates a discomfortable feeling against the wearer. Furthermore, the crotch region may be irregular folded and/or formed with a plurality of irregular creases as the crotch region of the diaper is squeezed between the wearer's thighs. As a result, a body discharge absorbing function expected to the crotch region is apt to be deteriorated and body discharges may leak beyond the crotch region of the diaper.

None of the processes as have exemplarily been disclosed above includes means for folding the crotch region of the diaper and therefore the diapers made by these processes are still accompanied with the problems as have been described above.

SUMMARY OF THE INVENTION

It is an object of the present invention is to provide the apparatus and the process for folding disposable diapers in their crotch regions and thereby to solve the problems as have been described above.

According to one aspect of the invention, there is provided an apparatus for folding and tucking a contiguous diaper structure running in a machine direction, the contiguous diaper structure including a plurality of crotch regions arranged at regular intervals in the machine direction and a plurality of first and second waist regions lying both sides of the crotch regions in a cross direction orthogonal to the machine direction and having a plurality of leg-holes each formed between each pair of the crotch regions adjacent to each other. The apparatus comprises a conveyor mechanism folding the contiguous diaper structure along a fold in the crotch region so that the first and second waist regions are oppositely spaced apart from each other and conveying the contiguous diaper structure in the machine direction with the contiguous diaper structure kept folded, a folding mechanism tucking the crotch region of the contiguous diaper structure into the inside of the contiguous diaper structure from the leg-holes lying on both sides of the crotch region, the folding mechanism including folding plates adapted to move toward and away from the crotch region of the contiguous diaper structure in the cross direction in synchronization with running of the contiguous diaper structure in the machine direction, each of the folding plates comprising a first base and a pair of guide arms extending from the first base in the cross direction and aligned in the machine direction, and the guide arms moving into the inside of the contiguous diaper structure as the folding plate moves toward the crotch region of the contiguous diaper structure, and then the guide arms catch opposite side edges of the crotch region in the vicinity of the fold from the outer side.

The apparatus according to the present invention includes the following embodiments.

Each of the guide arms has a proximal end and a distal end, the proximal end is fixed to the first base and the distal end repeatedly swing back and forth so that the opposite side edges of the guide arms get near to each other as the guide arms move into the contiguous diaper structure and get away from each other as the guide arms retract from the contiguous diaper structure.

The folding mechanism includes a first rotary disc adapted to rotate around an axis extending in a vertical direction, a plurality of the folding plates are arranged in a peripheral zone of the first rotary disc at regular intervals and mounted thereon by means of an axis extending in the vertical direction so as to rotate around the axis, the folding plates rotate around the axis of the first rotary disc as the first rotary disc rotates around its own axis and each of the folding plates rotates around its own axis by 360° while the first rotary disc around its own axis by 360° so that the direction to which the guide arms are opposed is always the same during rotation of the folding plates and the pair of the guide arms moves in the cross direction into the contiguous diaper structure to catch and press the crotch region of the contiguous diaper structure as the crotch region of the contiguous diaper structure gets nearer to the peripheral zone of the first rotary disc and moves in the cross direction apart from the contiguous diaper structure as the contiguous diaper structure gets away from the peripheral zone of the first rotary disc.

The folding mechanism includes a plurality of positive motion cams arranged in the peripheral zone of the first rotary disc at regular intervals and fixed thereon, each of the folding plates comprises links mounted on the proximal ends of the guide arms, a rod connected to the guide arms by means of the link and extending in the cross direction and a pin extending through an end zone of the rod and the first base in the vertical direction, the pin is slidably inserted into an eccentric cam groove of the positive motion cam and each of the positive motion cams rotates around the axis of the first rotary disc due to rotation of the first rotary disc and the pin moves along the cam groove so that the rod moves back and forth in the cross direction and the guide arms swing back and forth in the machine direction by means of the links and thereby the distal ends of the guide arms repeatedly get near to and away from each other.

The folding mechanism includes a plurality of auxiliary plates located so as to be opposed to the folding plates and adapted to move toward and away from the crotch region of the contiguous diaper structure between the first and second waist regions oppositely spaced apart from each other in synchronization with running of the contiguous diaper structure in the machine direction, each of the auxiliary plates comprises a second base and a pair of guide blades arranged side by side in the vertical direction and extending from the second base in the cross direction, each of the guide blades has a distal end tapered toward the cross direction, the guide arms and the guide blades synchronously move into the contiguous diaper structure and simultaneously the guide arms move into a clearance defined between the pair of the guide blades so that the crotch region is held between the guide arms and the guide blades and thereby tucked into the inside of the contiguous diaper structure.

The folding mechanism includes a second rotary disc located so as to be opposed to the first rotary disc and adapted to rotate around an axis extending in the vertical direction, a plurality of the auxiliary plates are arranged in a peripheral zone of the second rotary disc at regular intervals and mounted thereon by means of an axis extending through the second base in the vertical direction so as to rotate around the axis, the auxiliary plates rotate around the axis of the second rotary disc as the second rotary disc rotates around its own axis and each of the auxiliary plates rotates around its own axis by 360° while the second rotary disc rotates around its own axis by 360° so that the direction to which the guide blades are opposed is always the same during rotation of the auxiliary plate and each of the guide blades moves in the cross direction into the contiguous diaper structure between the first and second waist regions as the crotch region of the contiguous diaper structure gets nearer to the first and second rotary discs and moves in the cross direction apart from the contiguous diaper structure as the contiguous diaper structure gets away from the first and second rotary discs.

The contiguous diaper structure comprises a liquid-pervious continuous first web, a liquid-impervious continuous second web and a plurality of liquid-absorbent cores each interposed between the first and second webs and extending from the crotch region toward the first and second waist region in the cross direction.

According to another aspect of the present invention, there is provided a method for folding and tucking a contiguous diaper structure running in a machine direction, the contiguous diaper structure including a plurality of crotch regions arranged at regular intervals in the machine direction and a plurality of first and second waist regions lying both sides of the crotch regions in a cross direction orthogonal to the machine direction and having a plurality of leg-holes each formed between each pair of the crotch regions adjacent to each other. The method comprises the steps of folding the contiguous diaper structure along a fold in the crotch region so that the first and second waist regions are oppositely spaced apart from each other by conveyer means, folding and tucking the crotch region of the contiguous diaper structure into the inside of the contiguous diaper structure from the leg-holes lying on both sides of the crotch region by folding means. The folding means includes folding plates adapted to move toward and away from the crotch region of the contiguous diaper structure in the cross direction in synchronization with running of the contiguous diaper structure in the machine direction. Each of the folding plates comprises a first base and a pair of guide arms extending from the first base in the cross direction and aligned in the machine direction. The guide arms move into the inside of the contiguous diaper structure as the folding plate moves toward the crotch region of the contiguous diaper structure, and then the guide arms catch opposite side edges of the crotch region in the vicinity of the fold from the outer side.

The method according to the present invention includes the following embodiments.

Each of the guide arms has a proximal end and a distal end, the proximal end is fixed to the first base and the distal end repeatedly swing back and forth so that the opposite side edges of the guide arms get near to each other as the guide arms move into the contiguous diaper structure and get away from each other as the guide arms retract from the contiguous diaper structure.

The folding means include a first rotary disc adapted to rotate around an axis extending in a vertical direction, a plurality of the folding plates are arranged in a peripheral zone of the first rotary disc at regular intervals and mounted thereon by means of an axis extending in the vertical direction so as to rotate around the axis, the folding plates rotate around the axis of the first rotary disc as the first rotary disc rotates around its own axis and each of the folding plates rotates around its own axis by 360° while the first rotary disc rotates around its own axis by 360° so that the direction to which the guide arms are opposed is always the same during rotation of the folding plates and the pair of the guide arms moves in the cross direction into the contiguous diaper structure to catch and press the crotch region of the contiguous diaper structure as the crotch region of the contiguous diaper structure gets nearer to the peripheral zone of the first rotary disc and moves in the cross direction apart from the contiguous diaper structure as the contiguous diaper structure gets away from the peripheral zone of the first rotary disc, on the other hand.

The folding means include a plurality of positive motion cams arranged in the peripheral zone of the first rotary disc at regular intervals and fixed thereon, each of the folding plates comprises links mounted on the proximal end of the guide arms, a rod connected to the guide arms by means of the link and extending in the cross direction and a pin extending through an end zone of the rod and the first base in the vertical direction, the pin is slidably inserted into an eccentric cam groove of the positive motion cam and each of the positive motion cams rotates around the axis of the first rotary disc due to rotation of the fist rotary disc and the pin moves along the cam groove so that the rod moves back and forth in the cross direction and the guide arms swing back and forth in the machine direction by means of the links and thereby the distal ends of the guide arms repeatedly get near to and away from each other.

The folding means include a plurality of auxiliary plates located so as to be opposed to the folding plates and adapted to move toward and away from the crotch region of the contiguous diaper structure between the first and second waist regions oppositely spaced apart from each other in synchronization with running of the contiguous diaper structure in the machine direction, each of the auxiliary plates comprises a second base and a pair of guide blades arranged side by side in the cross direction and extending from the second base in the cross direction, each of the guide blades has a distal end tapered toward the cross direction, the guide arms and the guide blades synchronously move into the contiguous diaper structure and simultaneously the guide arms move into a clearance defined between the pair of the guide blades so that the transversely opposite side edge zones of the crotch region is held between the guide arms and the guide blades and thereby tucked into the inside of the contiguous diaper structure.

The folding means include a second rotary disc located so as to be opposed to the first rotary disc and adapted to rotate around an axis extending in the vertical direction, a plurality of the auxiliary plates are arranged in a peripheral zone of the second rotary disc at regular intervals and mounted thereon by means of an axis extending through the second base in the vertical direction so as to rotate around the axis, the auxiliary plates rotate around the axis of the second rotary disc as the second rotary disc rotates around its own axis and each of the auxiliary plates rotates around its own axis by 360° while the second rotary disc rotates around its own axis by 360° so that the direction to which the guide blades are opposed is always the same during rotation of the auxiliary plates and each of the guide blades moves in the cross direction into the contiguous diaper structure between the first and second waist regions as the crotch region of the contiguous diaper structure gets nearer to the first and second rotary discs and moves in the cross direction apart from the contiguous diaper structure as the contiguous diaper structure gets away from between the first and second rotary discs.

DETAILED DESCRIPTION OF THE PREFERRED EMBODIMENTS

Details in an apparatus and a process according to the present invention for folding disposable diapers in their crotch regions will be more fully understood from the description given hereunder with reference to the accompanying drawings.

Figure 1:
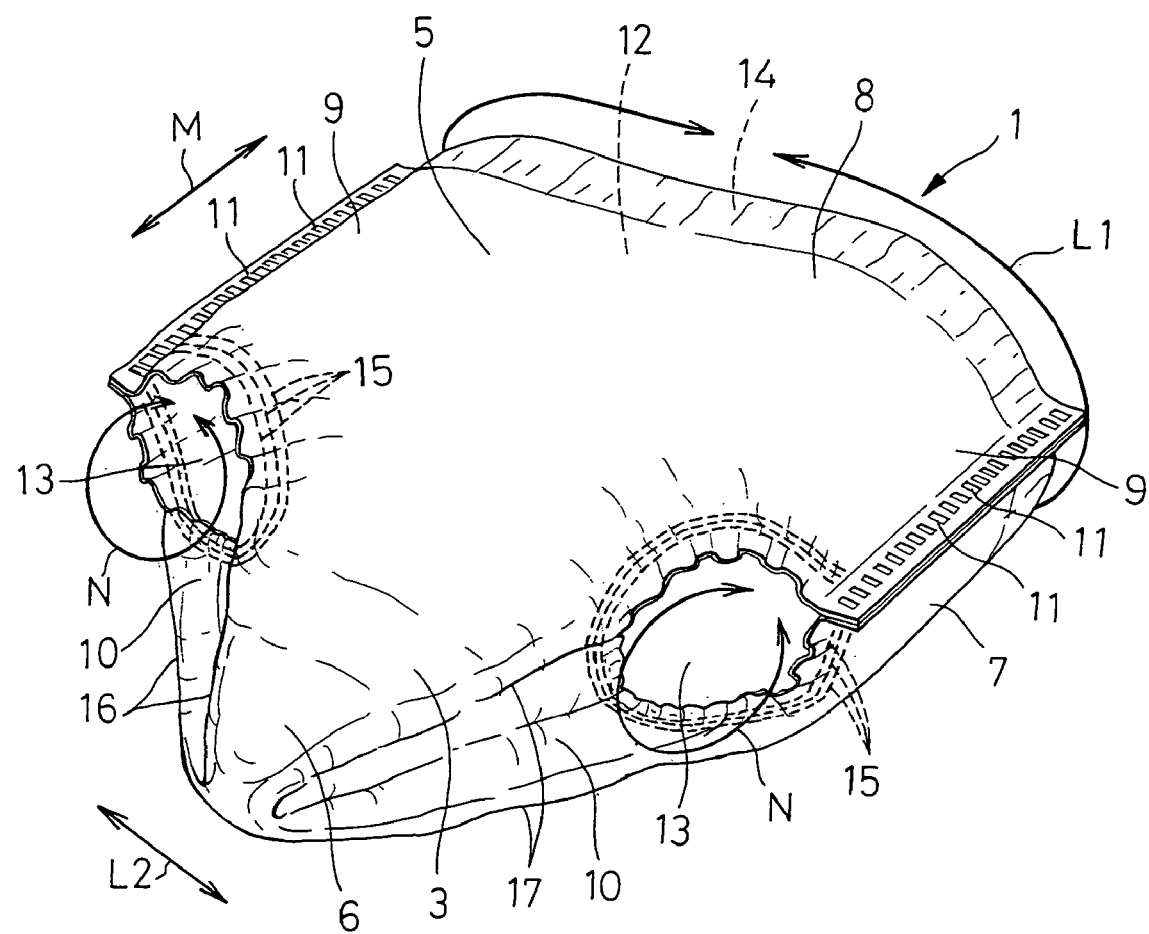
FIG. 1 is a perspective view showing an example of a pull-on diaper having its crotch region folded and tucked.
Figure 2:
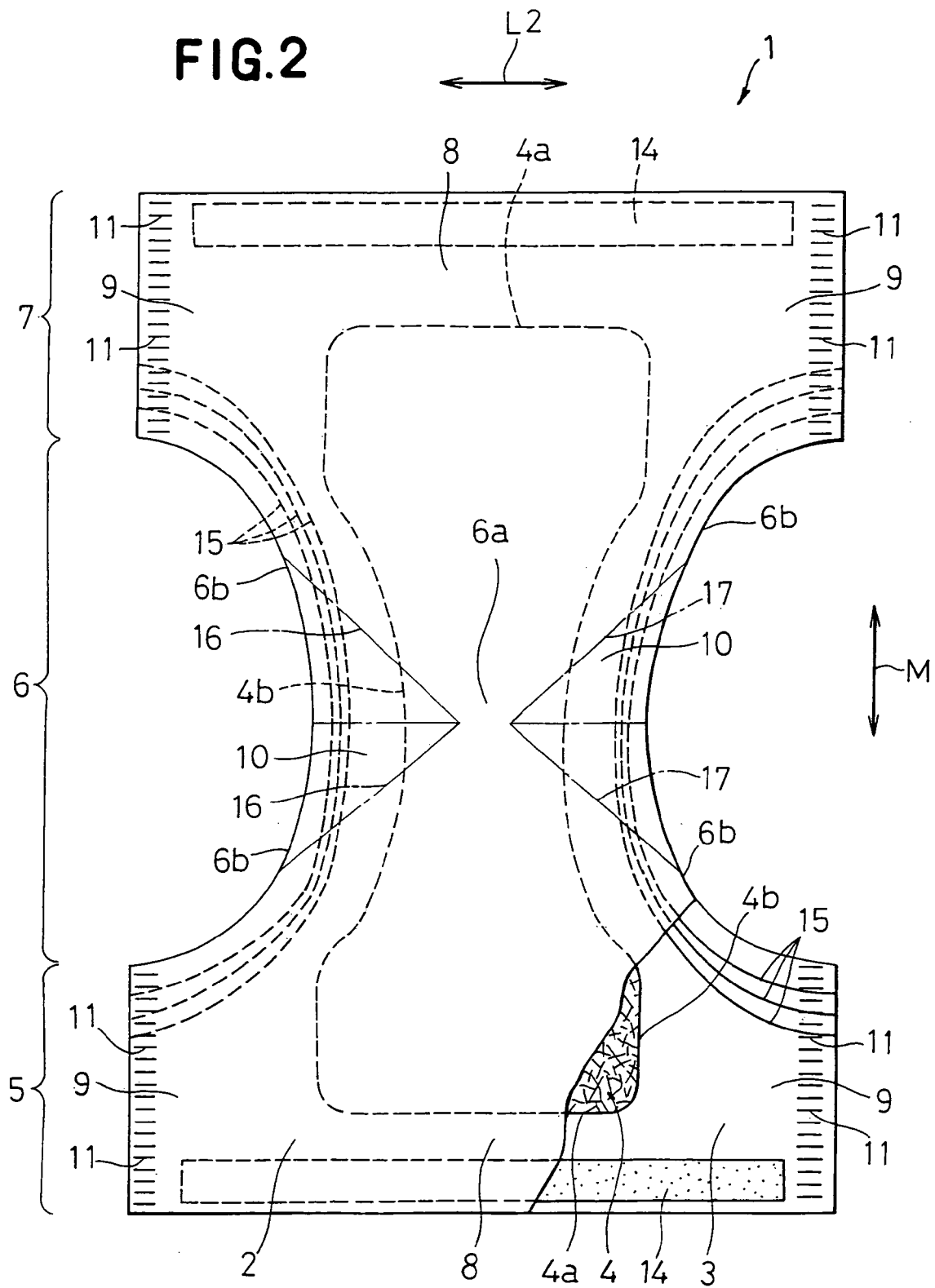
FIG. 2 is a partially cutaway developed plan view showing the diaper of FIG. 1.
Figure 3:
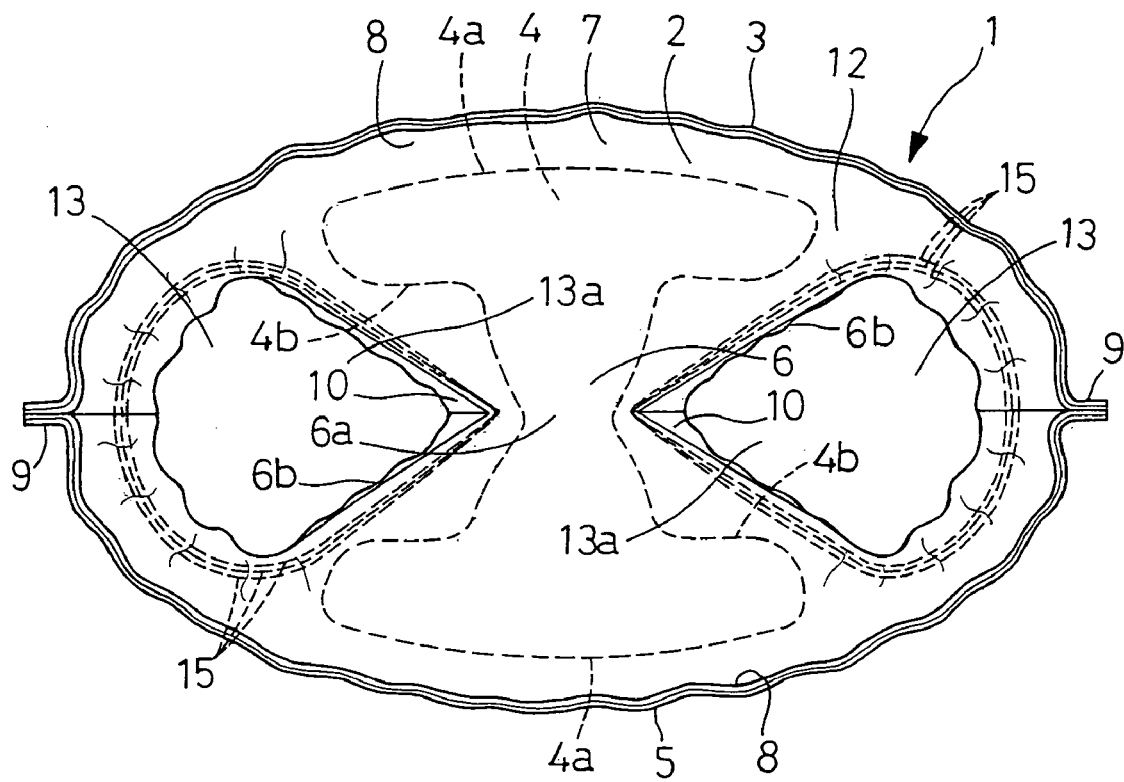
FIG. 3 is an overhead view showing the diaper of FIG. 1 from above the waist-hole.

FIG. 1 is a perspective view of a typical pull-on disposable diaper 1 having its crotch region 6 folded by an apparatus as will be described later, FIG. 2 is a partially cutaway developed plan view of the diaper 1 having front and rear waist regions 5, 7 disconnected from each other along transversely opposite side edge zones 9 thereof and FIG. 3 is an overhead view showing the diaper 1 from above a waist-hole 12. In FIGS. 1 and 2, a waist-circumferential direction is indicated by an arrow L1 (in FIG. 1 alone), a transverse direction is indicated by an arrow L2, a longitudinal direction is indicated by an arrow M and a thigh-circumferential direction is indicated by an arrow N (in FIG. 1 alone).

The diaper 1 comprises a liquid-pervious topsheet 2 (first web) facing the wearer's body, a liquid-impervious backsheet 3 (second web) facing away from the wearer's body and a liquid-absorbent core 4 interposed between the top- and backsheets 2, 3 and attached to at least one of these sheets 2, 3.

The diaper 1 is composed of the front waist region 5 (first or second waist region 81, 83), the rear waist region 7 (first or second waist region 81, 83) and the crotch region 6 (crotch region 82) extending between these waist regions 5, 7. The diaper 1 has longitudinally end zones 8 in the front and rear waist regions 5, 7 extending outside longitudinally opposite ends 4a of the core 4 in the waist-circumferential direction, transversely opposite side edge zones 9 of the respective waist regions 5, 7 extending outside transversely opposite side edges 4b of the core 4 in the longitudinal direction, and transversely opposite side edge zones 10 in the crotch region 6 destined to surround the wearer's thighs extending outside the side edges 4b of the core 4 in the thigh-circumferential direction. The core 4 extends almost entirely over the crotch region 6 and further extends into the front and rear waist regions 5, 7.

In the diaper 1, the side edge zones 9 in the respective waist regions are overlaid and joined together by means of a plurality of heat-sealing lines 11 arranged intermittently in the longitudinal direction. The diaper 1 is formed with a waist-hole 12 and a pair of leg-holes 13. In the crotch region 6, the side edge zones 10 destined to form the respective leg-holes 13 describe substantially circular arcs which are convex inwardly of the diaper 1. The diaper 1 has a transverse dimension smaller in the crotch region 6 than those in the front and rear waist regions 5, 7 so as to have a substantially hourglass-like planar shape in its developed state.

The end zones 8 are provided with band-like elastically stretchable members 14 extending in the waist-circumferential direction secured thereto, respectively, in a stretched state. The side edge zones 10 destined to form the leg-holes 13 are provided with a plurality of elastic members 15 secured thereto, respectively, in a stretched state. Along the end zones 8 and the side zones 9, 10, the top- and backsheets 2, 3 are overlaid and intermittently joined together.

As will be seen in FIG. 2, the diaper 1 is formed with a pair of first folding guide lines 16 and a pair of second folding guide lines 17 in the crotch region 6. The first folding guide lines 16 obliquely extend from a central zone 6a of the crotch region 6 to its one side edge 6b put aside toward the front and rear waist regions 5, 7, respectively so as to form a V-shape and the second folding guide lines 17 also obliquely extend from the central zone 6a of the crotch region 6 to its other side edge 6b put aside toward the front and rear waist regions 5, 6 to form a V-shape.

The diaper 1 is folded at the side edges 10 in the crotch region 6 inward in the transverse direction of the diaper 1 along the first and second folding guide lines 16, 17 and tucked into the inside of the diaper 1. In the crotch region 6, a dimension between the side edges 10 is correspondingly reduced.

Folding and tucking the diaper 1 at the side edges 10 in the crotch region 6 into the inside of the diaper 1 result in that the minimum transverse dimension of the diaper 1 in the crotch region 6 is substantially corresponds to the dimension between the side edges 10. In this way, it is possible to reduce the minimum transverse dimension in the crotch region 6 substantially corresponding to or even smaller than the transverse dimension of the wearer's crotch.

The diaper 1 fits the wearer's crotch in the crotch region 6 and therefore creates a discomfortable feeling against the wearer. Even when the diaper 1 is squeezed in the crotch region 6 by the wearer's crotch, there is no anxiety that the diaper 1 might be irregularly folded in the crotch region 6 or the core 4 might be formed with a plurality of irregular creases. In this way, body discharge absorbing capacity of the diaper 1 in the crotch region 6 is not deteriorated and any leakage of body discharges is reliably avoided.

As seen in FIG. 3, the waist-hole 12 and the bottoms 13a of the respective leg-holes 13 are substantially aligned with one another in a vertical direction, i.e., the bottoms 13a of the leg-holes 13 lie immediately below the waist-hole 12. The diaper 1 is free from an inconvenience that the wearer's toes and heels come up against the side edges 10 of the crotch region 6 as the wearer's legs are let through the waist-hole 12 and the leg-holes 13 when the diaper is put on the wearer's body. Therefore, it is not likely that a much time might be taken to put the diaper on the wearer's body.

Figure 4:
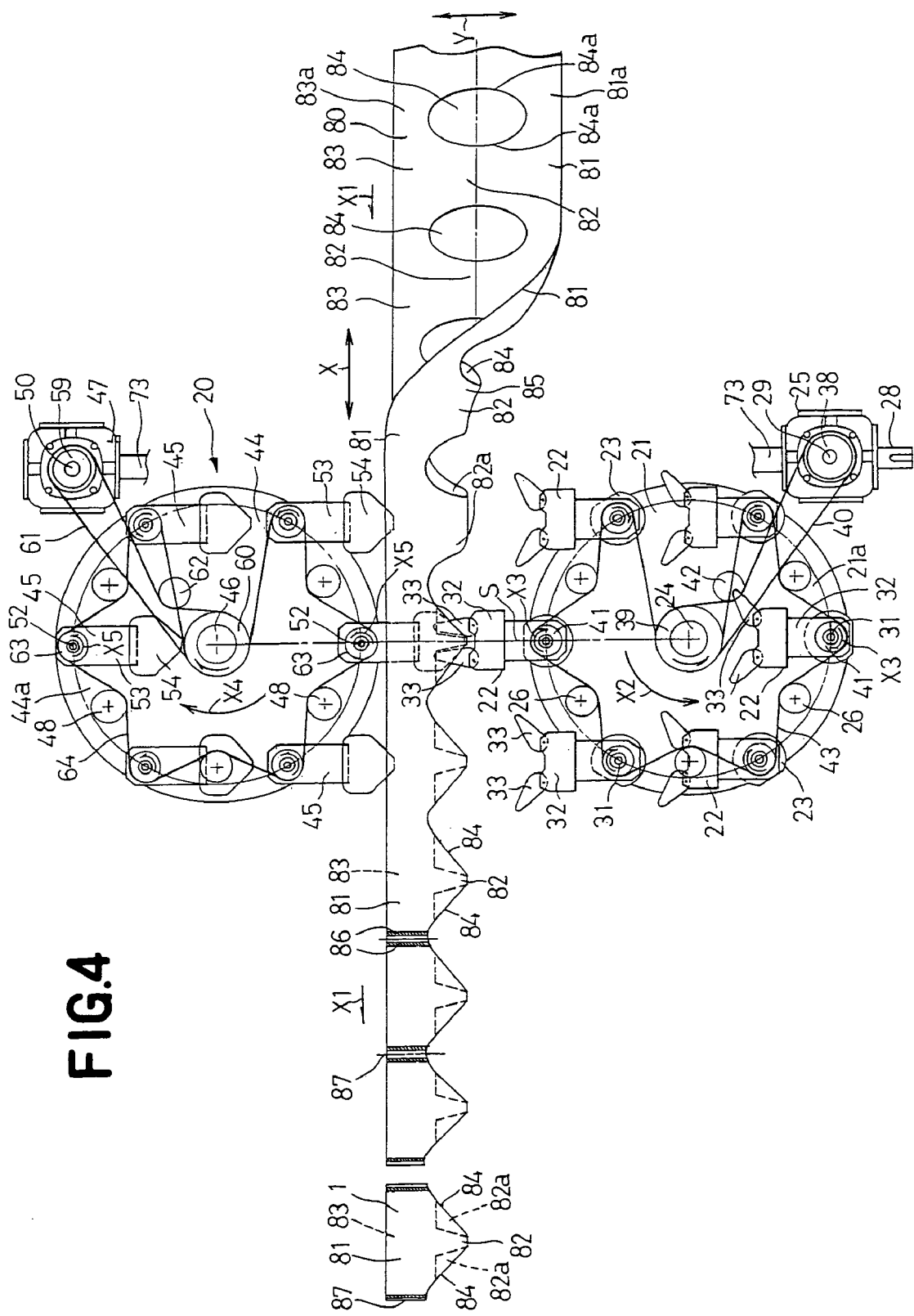
FIG. 4 is an overhead view showing an example of the apparatus for folding and tucking the diaper in the crotch region.
Figure 5:
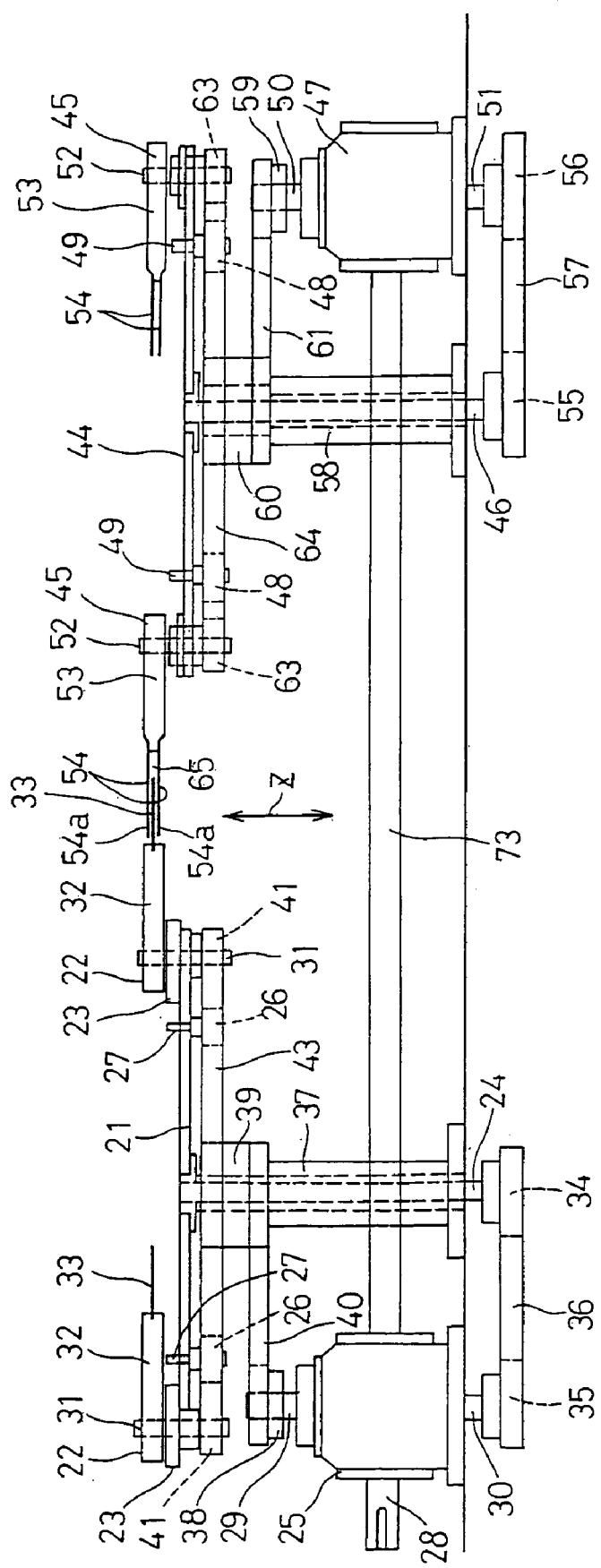
FIG. 5 is a side view corresponding to FIG. 4 showing the apparatus for folding and tucking the diaper in the crotch region.
Figure 6:
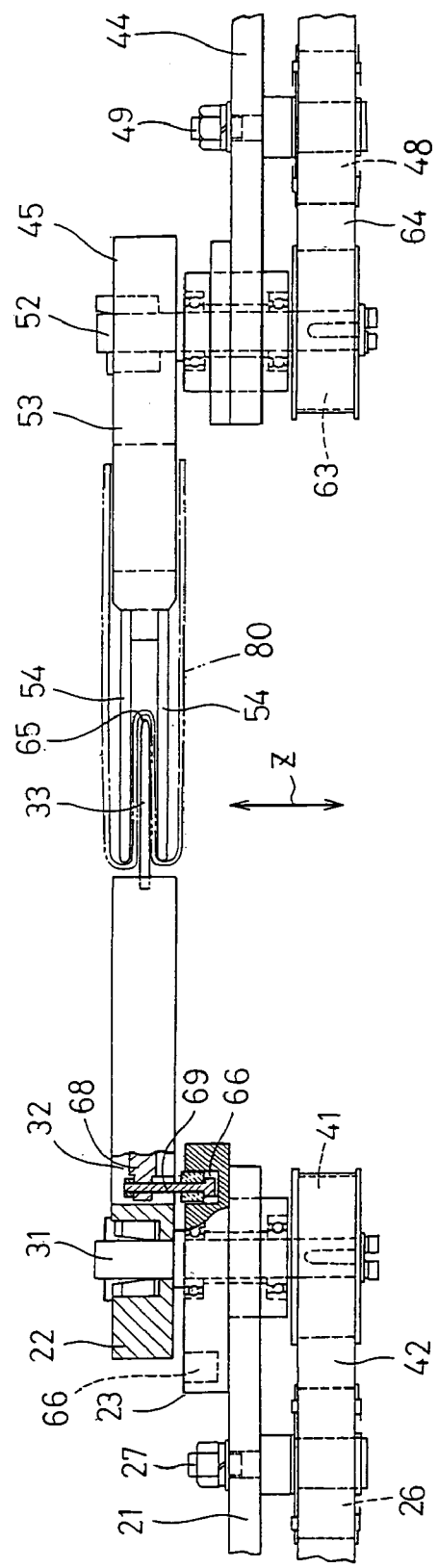
FIG. 6 is a partially cutaway scale-enlarged side view showing a part of FIG. 5.

FIG. 4 is an overhead view showing an example of the apparatus 20 for folding and tucking the diapers in their crotch region, FIG. 5 is a side view corresponding to FIG. 4 showing the apparatus 20 and FIG. 6 is a partially cutaway scale-enlarged side view showing a part of FIG. 5. In FIG. 4, a machine direction is indicated by an arrow X and a cross direction orthogonal to the machine direction is indicated by an arrow Y. In FIGS. 5 and 6, a vertical direction (i.e., a thickness direction of a contiguous diaper structure 80 folded along a longitudinal folding guide line 85) is indicated by an arrow Z. In FIGS. 4, 5 and 6, illustration of the contiguous diaper structure 80 is simplified so that a first web and a second web can not be distinguished from each other and, the core, the waist-circumferential elastic members and the leg-circumferential elastic members are not shown.

The apparatus 20 has a conveyor mechanism (conveyor means) serving to convey the contiguous diaper structure 80 at a constant speed forward in a machine direction indicated by an arrow X1 and a folding mechanism (folding means) serving to fold down the contiguous diaper structure 80 in the crotch regions 82.

The contiguous diaper structure 80 comprises a liquid-pervious continuous first web (corresponding to the liquid-pervious topsheet 2), a liquid-impervious continuous second web (corresponding to the liquid-impervious backsheet 3) and a plurality of liquid-absorbent cores (corresponding to the liquid-absorbent core 4) interposed between these first and second webs and attached to at least one of these first and second webs. The contiguous diaper structure 80 has a plurality of crotch regions 82 (corresponding to the crotch region 6) arranged at regular intervals in the machine direction, a plurality of first waist regions 81 (corresponding to the front waist region 5 or the rear waist region 7) and second waist regions 83 (corresponding to the front waist region 5 or the rear waist region 7) lying on both sides of the respective crotch regions 82 in the cross direction and contiguous to one another, respectively, in the machine direction, and a plurality of leg-holes 84 each formed between each pair of the crotch regions 82 adjacent to each other and arranged at regular intervals in the machine direction. The leg-holes 84 are formed by cutting the first and second webs and each of the leg-holes 84 presents an elliptical shape having its major axis in the cross direction.

The core lies between each pair of the leg-holes 84 adjacent to each other and extends over the substantially entire crotch region 82 and further extends into the first and second waist regions 81, 83 in the cross direction. The first web and the second web are overlaid and intermittently joined together at their peripheral portions outward beyond the core.

Each of the leg-holes 84 is provided along its peripheral zone 84a with a plurality of elastic members (not shown) attached thereto in a stretched state. The first and second waist regions 81, 83 are provided along end zones 81a, 83a thereof with band-like elastic members (not shown) attached thereto in a stretched state (See FIGS. 1 and 2).

In the contiguous diaper structure 80, the core may be provided along its both side edges with well known leak-barrier sheets normally biased to rise above the first web. The contiguous diaper structure 80 may comprise the liquid-impervious continuous second web and a plurality of absorbent panels placed on the inner surface of the second web between the respective pairs of the adjacent leg-holes 84. In this case, each of the panels will comprise a liquid-pervious upper sheet, a liquid-impervious lower sheet and an absorbent core interposed between these upper and lower sheets.

The conveyor mechanism conveys the contiguous diaper structure 80 forward in the machine direction indicated by the arrow X1 and, in the course of conveyance, the contiguous diaper structure 80 is folded in the crotch region 82 along a fold 85 extending in the machine direction so that the first and second waist regions 81, 83 may be oppositely spaced apart from each other. Though not illustrated, the conveyor mechanism comprises a guide rail for folding the crotch region 82 and a plurality of driving rolls adapted to rotate so as to convey the contiguous diaper structure 80 forward in the machine direction. The contiguous diaper structure 80 is folded by the guide rail, being conveyed using the rotating driving rolls.

The contiguous diaper structure 80 being conveyed forward in the machine direction is under a predetermined tension exerted thereupon in the machine direction. After the contiguous diaper structure 80 in the crotch region 82 has been folded along the fold 85, such tension acts on the first and second waist regions 81, 83 but substantially does not act on the crotch region 82.

The folding mechanism comprises a first rotary disc 21 lying transversely outside the fold 85 of the contiguous diaper structure 80, six folding plates 22 mounted at regular intervals on the first rotary disc 21 along its peripheral zone 21*a* and six positive motion cams 23 mounted on the first rotary disc 21 along its peripheral zone 21*a* so as to be interposed between the first rotary disc 21 and the respective folding plates 22, a second rotary disc 44 located on the outer side of the first rotary disc 21 across the contiguous diaper structure 80 and six auxiliary plates 45 mounted on the second rotary disc 44 along its peripheral zone 44*a*. It should be understood that the number of these plates 22, 45 are not particularly specified while six folding plates 21 and six auxiliary plates 45 are exemplarily illustrated.

The first rotary disc 21 rotates around an axis 24 extending in a direction indicated by an arrow X2 so that the contiguous diaper structure 80 is conveyed forward in the machine direction indicated by the arrow X1. Outside the first rotary disc 21, there is provided a gear box 25 adapted to transmit a driving force to the first rotary disc 21 and the folding plates 22. The first rotary disc 21 is provided along its peripheral zone 21*a* with five guide wheels 26 each lying between each pair of the folding plates 22 adjacent to each other and mounted on the first rotary disc 21 by means of an axis 27 extending in the vertical direction. These guide wheels 26 are rotatable independently of the first rotary disc 21.

An axis 28 of the gear box 25 is rotationally driven by an electric motor (not shown). Within the gear box 25, there is provided a bevel gear (not shown) via which a rotation of the axis 28 is transmitted to an axis 29 extending upward from the gear box 25 in the vertical direction, an axis 30 extending downward from the gear box 25 in the vertical direction and a shaft 73.

Each of the folding plates 22 is mounted on the first rotary disc 21 by means of an axis 31 extending in the vertical direction so as to be rotatable independently of the first rotary disc 21. The folding plates 22 lie outside the fold 85 of the contiguous diaper structure 80 as viewed in the cross direction and arranged at regular intervals along the peripheral zone 21*a* of the first rotary disc 21. Similarly to these folding plates 22, the positive motion cams 23 are arranged at regular intervals along the peripheral zone 21*a* of the first rotary disc 21. Line segments extending from the axis 24 of the first rotary disc 21 to each of the axes 31 of the respective folding plates 22 are at an angle of 60°.

With an arrangement such that the first rotary disc 21 is provided along its peripheral zone 21*a* with three folding plates 22 at regular intervals, the line segments extending from the axis 24 of the first rotary disc 21 to each of the axes 31 of the respective folding plates 22 are at an angle of 120° and, with an arrangement such that the first rotary disc 21 is provided along its peripheral zone 21*a* with four folding plates 22 at regular intervals, the line segments extending from the axis 24 of the first rotary disc 21 to each of the axes 31 of the respective folding plates 22 are at an angle of 90°.

The folding plates 22 are adapted to move toward and away from the contiguous diaper structure 80 as the first rotary disc 21 rotates. Each of the folding plates 22 comprises a first base 32 and a pair of guide arms 33 extending from the first base 32 toward the contiguous diaper structure 80 in the cross direction.

The axis 24 of the first rotary disc 21 and the axis 30 of the gearbox 25 are provided with pulleys 34, 35, respectively. These axes 24, 30 are operatively associated with each other by means of open belt 36 guided by the pulleys 34, 35. Rotation of the axis 30 of the gear box 25 is transmitted to the axis 24 of the first rotary disc 21 via the open belt 36. Rotation of the axis 30 causes the first rotary disc 21 to rotate in the same direction indicated by the arrow X2 as the direction in which the axis 24 rotates.

The first rotary disc 21 is provided around its bearing 37 with a pulley 39 adapted to rotate independently of the axis 24. This pulley 39 is rotatably mounted on a bearing 37. The axis 24 is inserted into the bearing 37. The axis 29 of the gear box 25 is provided with a pulley 38. The axis 29 and the pulley 39 are operatively associated with each other via an open belt 40 guided by the pulleys 38, 39. Between the pulley 38 and the pulley 39, there are provided guide wheels 42 serving to keep the belt 40 under tension. The axes 31 of the respective folding plates 22 are provided with pulleys 41. The axes 31 and the pulley 39 are operatively associated with each other via belt 43 guided by the pulleys 39, 41.

More specifically, the belt 43 extends from the pulley 39 to one of the pulleys 41 associated with one of the folding plates 22 and further extends, via the guide wheels 26, to the pulley 41 associated with the adjacent folding plate 22. Rotation of the axis 29 is transmitted via the belt 40 to the pulley 39. Rotation of the pulley 39 is transmitted via the belt 43 to the axes 31 of the folding plates 22. Rotation of the axes 31 causes these folding plates 22 to rotate in a direction indicated by an arrow X3 opposed to the direction indicated by the arrow X2 in which the first rotary disc 21 rotates. In the course of such rotation, the belt 43 is maintained under tension by the guide wheels 26.

A pair of the guide arms 33 are arranged side by side in the machine direction and have respective inner side edges 33*a* opposed to each other and respective distal ends 33*b* adapted to swing back and forth in the machine direction. Each of the guide arms 33 is taper down to the distal end 33*b*. The inner side edges 33*a* opposed to each other are spaced apart from each other gradually toward the distal ends 33*b* (See FIG. 8). The guide arms 33 rotate so that respective distal ends 33*b* may repeatedly down near to and draw away from each other.

The second rotary disc 44 rotates around an axis 46 extending in a direction indicated by an arrow X4 so that the contiguous diaper structure 80 is conveyed forward in the machine direction indicated by the arrow X1. Outside the second rotary disc 44, there is provided a gear box 47 adapted to transmit a driving force to the second rotary disc 44 and the auxiliary plates 45. The second rotary disc 44 is provided along its peripheral zone 44*a* with five guide wheels 48 each lying between each pair of the auxiliary plates 45 adjacent to each other and mounted on the second rotary disc 44 by means of an axis 49 extending in the vertical direction. These guide wheels 48 are rotatable independently of the second rotary disc 44.

The gear box 25 and the gear box 47 are coupled to each other by means of a shaft 73. A rotational force is transmitted from the gear box 25 to the gear box 47 by means of the shaft 73. Within the gear box 47, there is provided a bevel gear (not shown) via which a rotation of the shaft 73 is transmitted to an axis 50 extending upward from the gear box 47 and an axis 51 extending downward from the gear box 47.

Each of the auxiliary plates 45 is mounted on the second rotary disc 44 by means of an axis 52 extending in the vertical direction so as to be rotatable independently of the second rotary disc 44. The auxiliary plates 45 lie outside the first and second waist regions 81, 83 of the contiguous diaper structure 80 and arranged at regular intervals along the peripheral zone 44*a* of the second rotary disc 44. Line segments extending from the axis 46 of the second rotary disc 44 to each of the axes 52 of the respective auxiliary plates 45 are at an angle of 60°.

With an arrangement such that the second rotary disc 44 is provided along its peripheral zone 44*a* with three auxiliary plates 45 at regular intervals, the line segments extending from the axis 46 of the second rotary disc 44 to each of the axes 52 of the respective auxiliary plates 45 are at an angle of 120° and, with an arrangement such that the second rotary disc 44 is provided along its peripheral zone 44*a* with four auxiliary plates 45 at regular intervals, the line segments extending from the axis 46 of the second rotary disc 44 to each of the axes 52 of the respective auxiliary plates 45 are at an angle of 90°.

The auxiliary plates 45 are adapted to move toward and away from the crotch region 82 of the contiguous diaper structure 80 through a clearance defined by the first and second waist regions 81, 83 oppositely spaced apart from each other as the second rotary disc 44 rotates. Each of the auxiliary plates 45 comprises a second base 53 and a pair of guide blades 54 extending from the second base 53 toward the contiguous diaper structure 80 in the cross direction.

The guide blades 54 horizontally extend in parallel to each other and have distal ends 54*a* tapered from the second base 53 toward the contiguous diaper structure 80. Between these guide blades 54, a clearance 65 is defined, which has a predetermined dimension sufficient to receive the associated folding plate 22.

The axis 46 of the second rotary disc 44 and the axis 51 of the gear box 47 are provided with pulleys 55, 56, respectively. These axes 46, 51 are operatively associated with each other by means of open belt 57 guided by these pulleys 55, 56. Rotation of the axis 51 of the gear box 47 is transmitted to the axis 46 of the second rotary disc 44 via the open belt 57. Rotation of the axis 46 causes the second rotary disc 44 to rotate in the same direction indicated by the arrow X4 as the direction in which the axis 46 of the second rotary disc 44 rotates.

The second rotary disc 44 is provided around its bearing 58 with a pulley 60 adapted to rotate independently of the axis 46. This pulley 60 is rotatably mounted on the bearing 58. The axis 46 is inserted into the bearing 58. The axis 50 of the gear box 47 is provided with a pulley 59. The axis 50 and the pulley 60 are operatively associated with each other via open belt 61 guided by the pulleys 59, 60. Between the pulley 59 and the pulley 60, there are provided guide wheels 62 serving to keep the belt 61 under tension. The axes 52 of the respective auxiliary plates 45 are provided with pulleys 64. The axes 52 and the pulley 60 are operatively associated with each other via belt 64 guided by the pulleys 60, 63.

More specifically, the belt 64 extends from the pulley 60 to one of the pulleys 63 associated with one of the auxiliary plates 45 and further extends, via the guide wheels 48, to the pulley 63 associated with the adjacent auxiliary plate 45. Rotation of the axis 50 is transmitted via the belt 61 to the pulley 60. Rotation of the pulley 60 is transmitted via the belt 64 to the axes 52 of the auxiliary plates 45. Rotation of the axes 52 causes these auxiliary plates 45 to rotate in a direction indicated by an arrow X5 opposed to the direction indicated by the arrow X4 in which the second rotary disc 44 rotates. In the course of such rotation, the belt 64 is maintained under tension by these guide wheels 48.

The contiguous diaper structure 80 is folded and tucked in the crotch regions 82 by such apparatus 20 in the following manner. The contiguous diaper structure 80 is folded along the fold 85 as the contiguous diaper structure 80 is conveyed forward in the machine direction indicated by the arrow X1 by the conveyor mechanism. The contiguous diaper structure 80 with the first and second waist regions 81, 83 oppositely spaced apart from each other is guided between the first and second rotary discs 21, 44. The first and second rotary discs 21, 44 are rotating in the direction indicated by the arrow X2 and the arrow X4, respectively, in syncronization with the running speed of the contiguous diaper structure 80.

In the apparatus 20, the guide arms 33 extending from one of the folding plates 22 progressively move into the contiguous diaper structure 80 in the vicinity of a pair of the leg-holes 84 lying on the both sides of the crotch region 82 as the crotch region 82 of the contiguous diaper structure 80 gets nearer to the first and second rotary discs 21, 44. In synchronization with the guide arms 33 of the folding plate 22, the guide blades 54 extending from one of the auxiliary plates 45 progressively move into the inside of the contiguous diaper structure 80 through a clearance defined by the first and second waist regions 81, 83 oppositely spaced apart from each other.

As the crotch region 82 of the contiguous diaper structure 80 gets nearer to an imaginary line S extending between the axes 24, 46 of the respective rotary discs 21, 44, the opposite side edges 33*a* of the guide arms 33 having moved into the contiguous diaper structure 80 come in contact with the crotch region 82 from its outer side and the guide arms 33 swing inward so that the distal ends 33*b* of the respective guide arms 33 may get close to each other. In this way, the guide arms 33 catch side edge zones 82*a* of the crotch region 82 extending in the vicinity of the fold 85 between the opposite side edges 33*a* thereof so as to press these side edge zones 82*a* into the inside of the contiguous diaper structure 80. Simultaneously, the guide arms 33 move into the clearance 65 defined between the guide blades 54 so that the side edge zones 82*a* may be held between the guide arms 33 and the guide blades 54 and thereby tucked into the inside of the contiguous diaper structure 80.

In the apparatus 20, the guide arms 33 swing so that the distal ends 33*b* may be spaced apart from each other as the crotch region 82 of the contiguous diaper structure 80 move away from the first and second rotary discs 21, 44. Thereupon the guide arms 33 progressively retract from the contiguous diaper structure 80. The guide blades 54 of the auxiliary plate 45 progressively retract from the contiguous diaper structure 80 in syncronization with the guide arms 33 of the folding plate 22. The contiguous diaper structure 80 with the crotch region 82 thus folded and tucked runs through the clearance between the first and second rotary discs 21, 44 in the machine direction.

In the contiguous diaper structure 80 folded in the crotch region 82 along the fold 85, the crotch region 82 is substantially free from affection of the tension exerted upon the first and second waist regions 81, 83, so the side edge zones 82*a* of the crotch region 82 can be easily tucked and, in addition, the contiguous diaper structure 80 can be conveyed forward in the machine direction with the crotch region 82 reliably kept in a tucked state.

After the side edge zones 82*a* of the crotch region 82 have been tucked inward, the first and second waist regions 81, 83 oppositely spaced apart from each other now overlap each other and then the first and second webs are joined by means of two heat-sealing lines 86 extending in the cross direction. These heat-sealing lines 86 are formed so that the individual diaper 1 may have a symmetrical appearance. Subsequently, the first and second webs are cut along cutting lines 87 each extending in the cross direction between two sets of the heat-sealing lines 86 adjacent to each other. These cutting lines 87 extend across the first and second waist regions 81, 83 in the cross direction. The contiguous diaper structure 80 is cut along the respective cutting lines 87 to obtain a plurality of the individual diapers 1 shown in FIG. 1 which are arranged side by side in the machine direction.

This apparatus 20 arrows the contiguous diaper structure 80 in the crotch region 82 to be continuously and rapidly folded and tucked inward. Furthermore, the apparatus 20 allows the side edge zone 82a of the crotch region 82 to be reliably folded and tucked inward since the guide arms 33 catch the side edge zones 82a to press these side edge zones 82a into the inside of the contiguous diaper structure 80 and simultaneously the guide arms 33 move into the clearance 65 between the guide blades 54 to hold the side edge zones 82a between the guide arms 33 and the guide blades 54.

Figure 7:
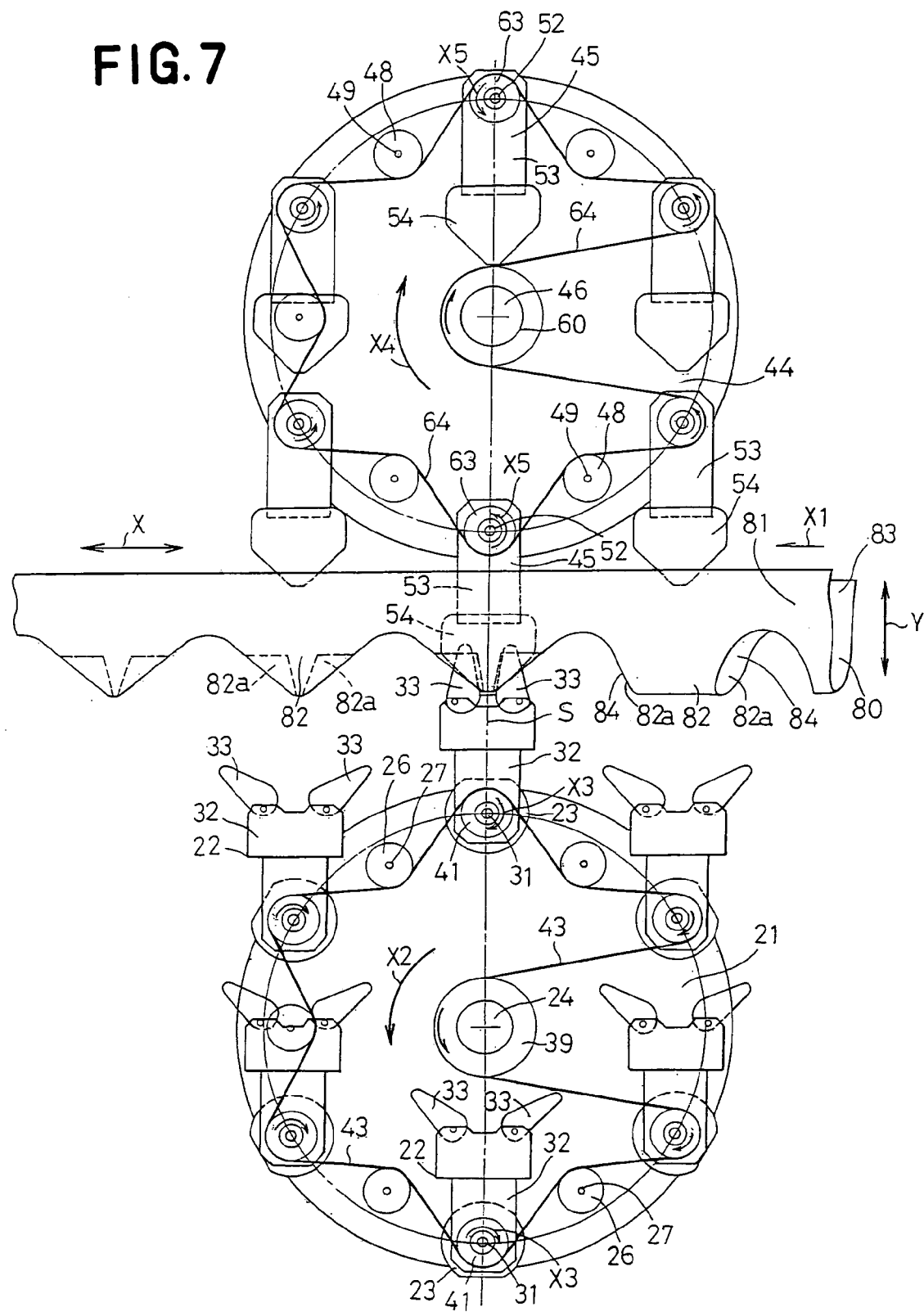
FIG. 7 is an overhead view of first and second rotary discs in which a contiguous diaper structure and an electric motor are not shown.

FIG. 7 is an overhead view of the first and second rotary discs 21, 44. In the apparatus 20, the first rotary disc 21 rotates in the direction of the arrow X2 around the axis 24 and the folding plates 22 rotate around the axis 24 of the first rotary disc 21 accordingly. At the same time, each of the folding plates 22 rotates in the peripheral zone 21a of the first rotary disc 21 around the axes 31 thereof in the direction of the arrow X3 opposite to the direction of the arrow X2 in which the first rotary disc 21 rotates. Each of the folding plates 22 rotates by 360° rotation around the axis 31 in the peripheral zone 21a of the first rotary disc 21 while the folding plates 21 rotate by 360° around the axis 24 of the first rotary disc 21 due to rotation of the first rotary disc 21. Consequently, the direction in which the guide arms 33 are opposed to the contiguous diaper structure 80 are always the same. More specifically, in the course of rotation of the folding plates 22 around the axis 24 of the first rotary disc 21, the guide arms 33 always face to the cross direction and there is no possibility that the guide arms 33 might turn to the machine.

In the apparatus 20, the second rotary disc 44 rotates in the direction of the arrow X4 around the axis 46 and the auxiliary plates 45 rotate around the axis 46 of the second rotary disc 44 accordingly. At the same time, each of the auxiliary plates 45 rotates in the peripheral zone 44a of the second rotary disc 44 around the axes 52 thereof in the direction of the arrow X5 opposite to the direction of the arrow X5 in which the second rotary disc 44 rotates. Each of the auxiliary plates 45 rotates by 360° around the axis 52 in the peripheral zone 44a of the second rotary disc 44 while the auxiliary plates 45 rotate by 360° around the axis 46 of the second rotary disc 44 due to rotation of the second rotary disc 44. Consequently, the direction in which the guide blades 54 are opposed to the contiguous diaper structure 80 are always the same. More specifically, in the course of rotation of the auxiliary plates 54 around the axis 46 of the second rotary disc 44, the guide blades 54 always face to the cross direction and there is no possibility that the guide blades 54 might turn to the machine direction.

Figure 8:
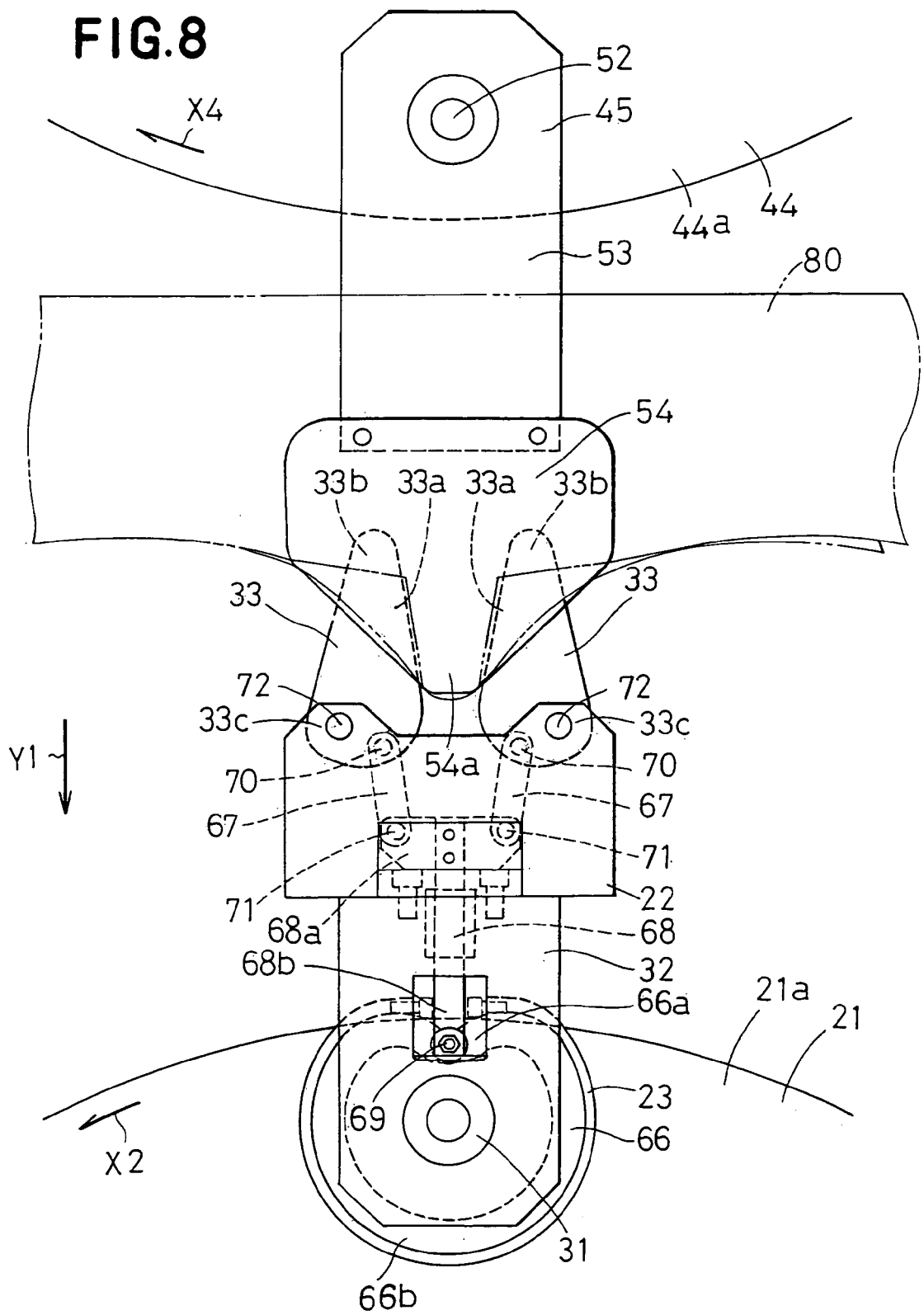
FIG. 8 is a scale-enlarged overhead view of a folding plate and an auxiliary plate.
Figure 9:
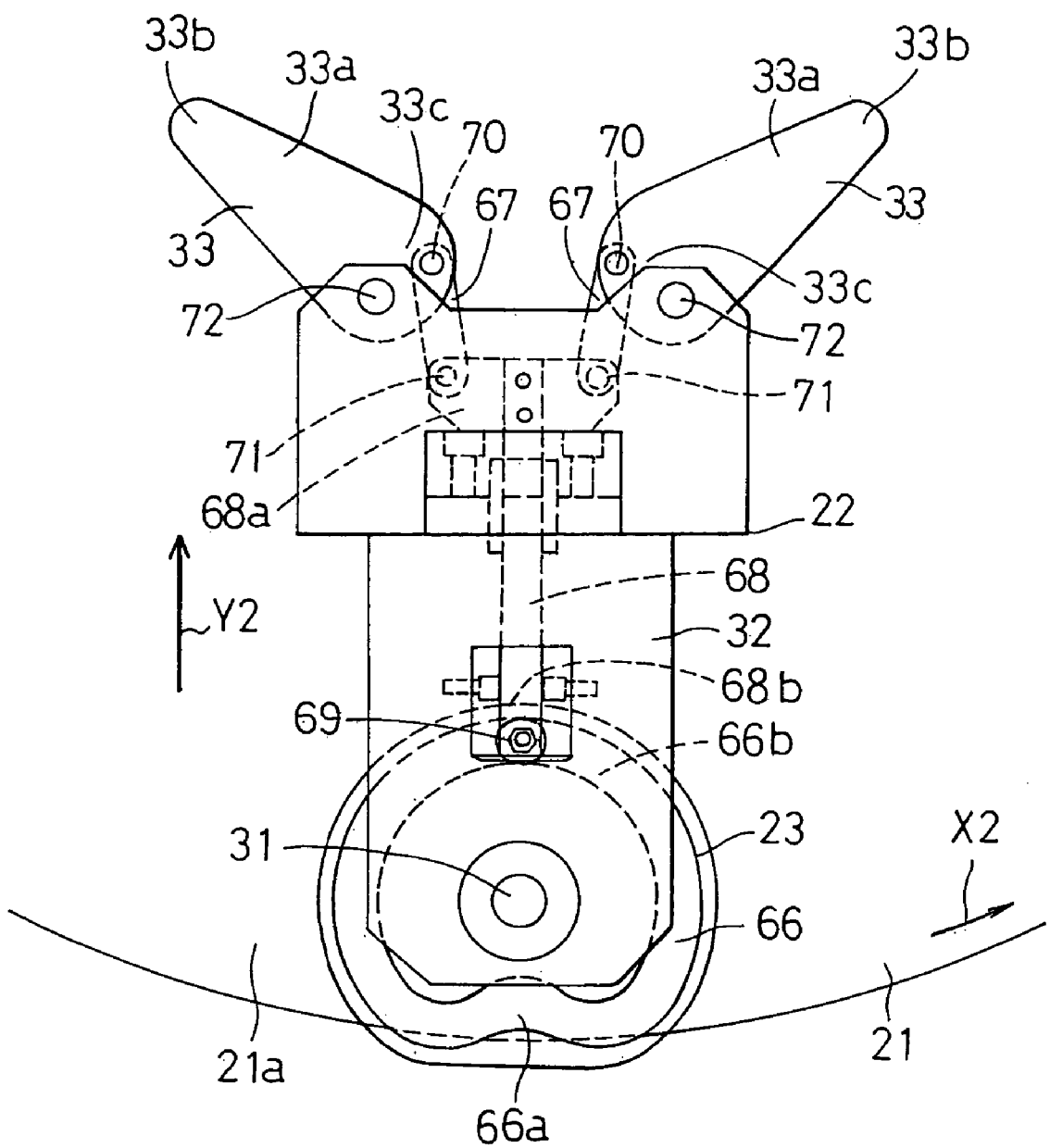
FIG. 9 is a scale-enlarged overhead view of the folding plate.

FIG. 8 is a scale-enlarged overhead view of the folding plate 22 and the auxiliary plate 45 and FIG. 9 is a scale-enlarged overhead view of the folding plate 22. In FIG. 8, the guide arms 33 are illustrated as having moved into the clearance 65 between the guide blades 54. FIG. 9 illustrates the folding plate 22 after the first rotary disc 21 has rotated from its position in FIG. 8 by 180°.

The positive motion cams 23 are interposed between the first rotary disc 21 and the first bases 32 of the respective folding plates 22 and fixed to the first rotary disc 21. Each of the positive motion cams 23 is formed with an eccentric cam groove 66. The cam groove 66 is defined by a depressed zone 66a sloping down toward the axis 31 of the folding plate 22 and a circular zone 66b extending around a peripheral edge of the positive motion cam 23.

Each of the folding plates 22 has a pair of links 67 mounted on proximal end zones 33c of the guide arms 33, a rod 68 connected to the links 67 and a pin 69 lying in a rear end zone 68b (end zone) of the rod 68 and extending in the vertical direction. The links 67 and the rod 68 extend from the proximal end zones 33c of the guide arms 33 toward the first base 32 in the cross direction. The links 67 are mounted on axes 70 provided in the proximal end zones 33c of the guide arms 33 and on axes 71 lying in a front end zone 68a of the rod 68. The guide arms 33 have the proximal end zones 33c mounted on the first base 32 by means of pivot pins 72. The pin 69 is slidably inserted in the cam groove 66 of the positive motion cam 23.

The positive motion cams 23 rotate around the axis 24 of the first rotary disc 21 due to rotation of the first rotary disc 21 and the pin 69 moves along the cam groove 66 as the first rotary disc 21 rotates. Movement of the pin 69 along the cam groove 66 causes the rod 68 to move back and forth in the cross direction and the guide arms 33 swing back and forth in the machine direction so that the distal ends 33b of the respective guide arms 33 may repeatedly move toward and away from each other accordingly.

When one of the folding plates 22 is opposed to one of the auxiliary plates 45 as shown in FIG. 8, the pin 69 is positioned in the zone 66a of the cam groove 66 and the rod 68 retracts in the cross direction indicated by the arrow Y1 toward the axis 31 of this folding plate 22. Retraction of the rod 68 causes one of the guide arms 33 to swing forward in the machine direction and the other guide arm 33 to swing backward in the machine direction both by means of the links 67 so that the opposite side edge zones 33a of these guide arms 33 may get nearer to each other. Thereupon, the guide arms 33 move into the clearance 65 between the guide blades 54.

180° rotation of the first rotary disc 21 from the position shown in FIG. 8 causes the pin 69 to be positioned in the zone 66b of the cam groove 66 as shown in FIG. 9 and thereby causes the rod 68 to move forward in the cross direction indicated by the arrow Y2. Upon movement forward of the rod 68, one of the guide arms 33 swings backward in the machine direction and the other guide arm 33 swings forward in the machine direction both by means of the links 67 so that the opposite side edge zones 33a of these guide arms 33 may draw away from each other.

Figure 10:
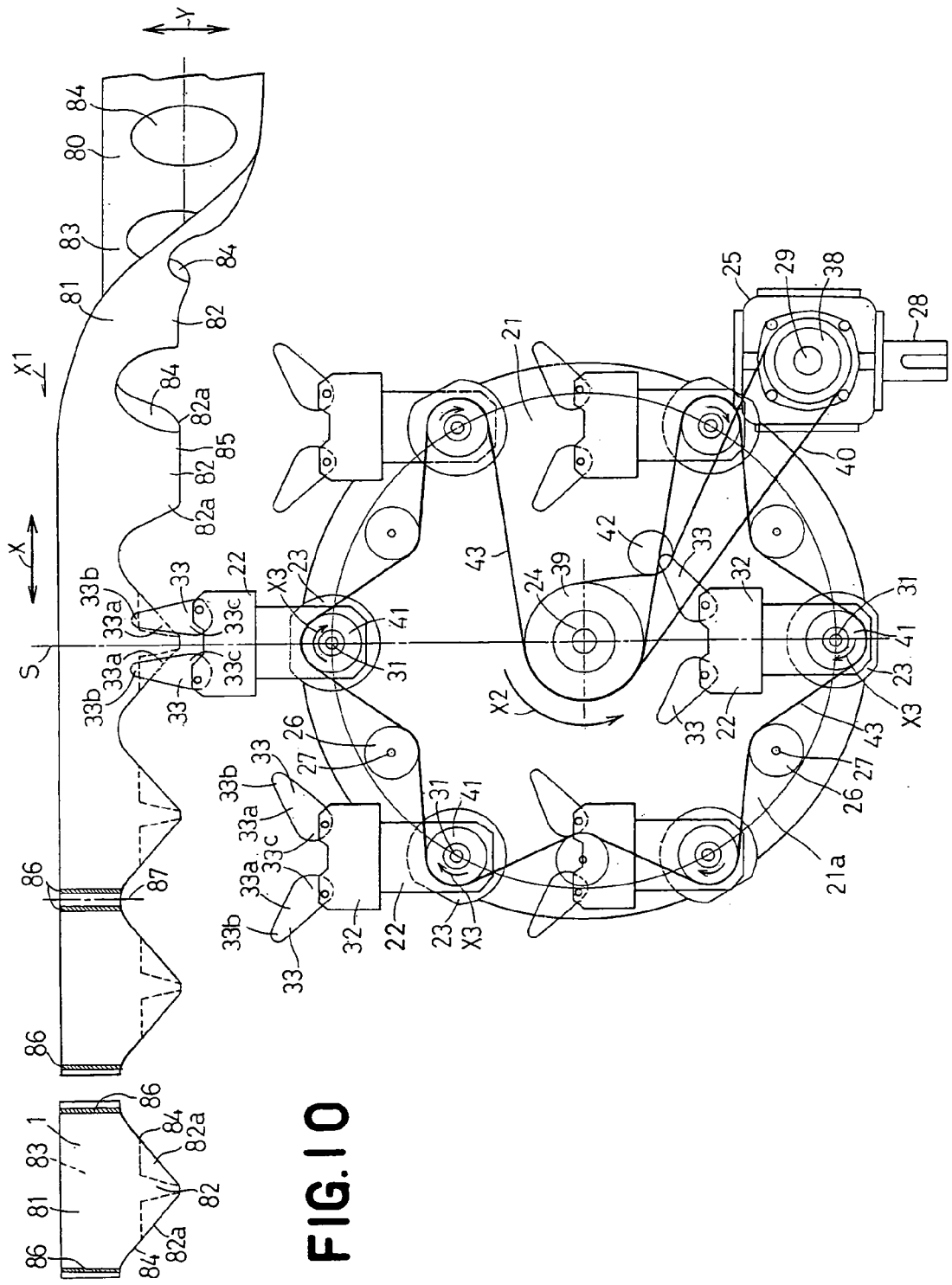
FIG. 10 is an overhead view showing another example of the apparatus for folding and tucking the diaper in the crotch region.
Figure 11:
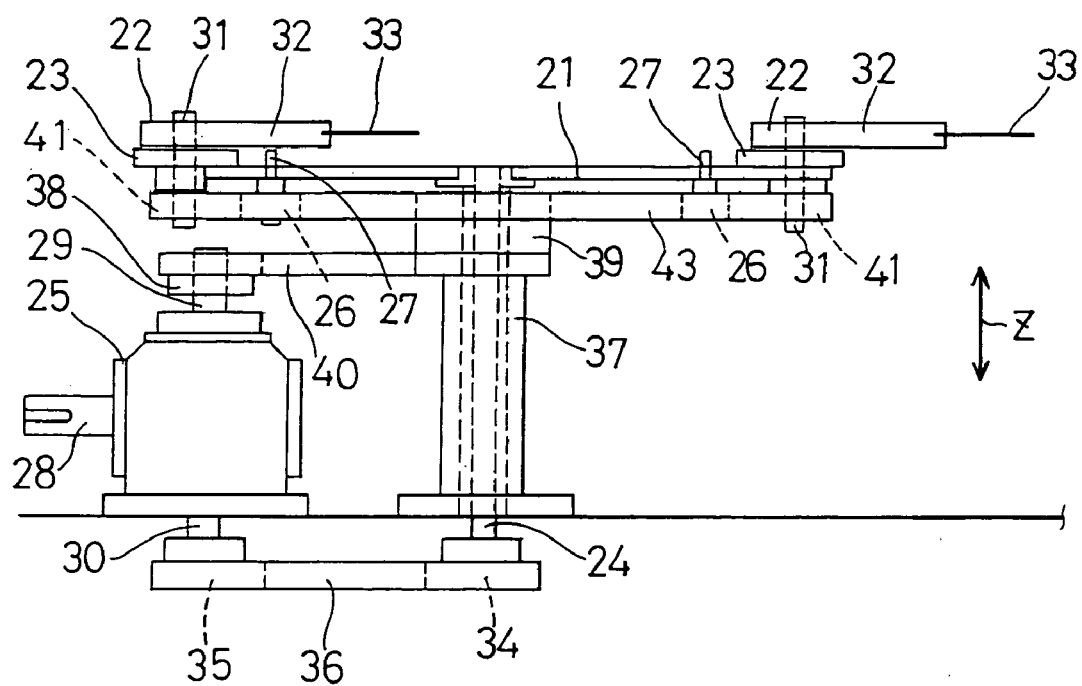
FIG. 11 is a side view corresponding to FIG. 10 showing the apparatus for folding and tucking the diaper in the crotch region.
Figure 12:
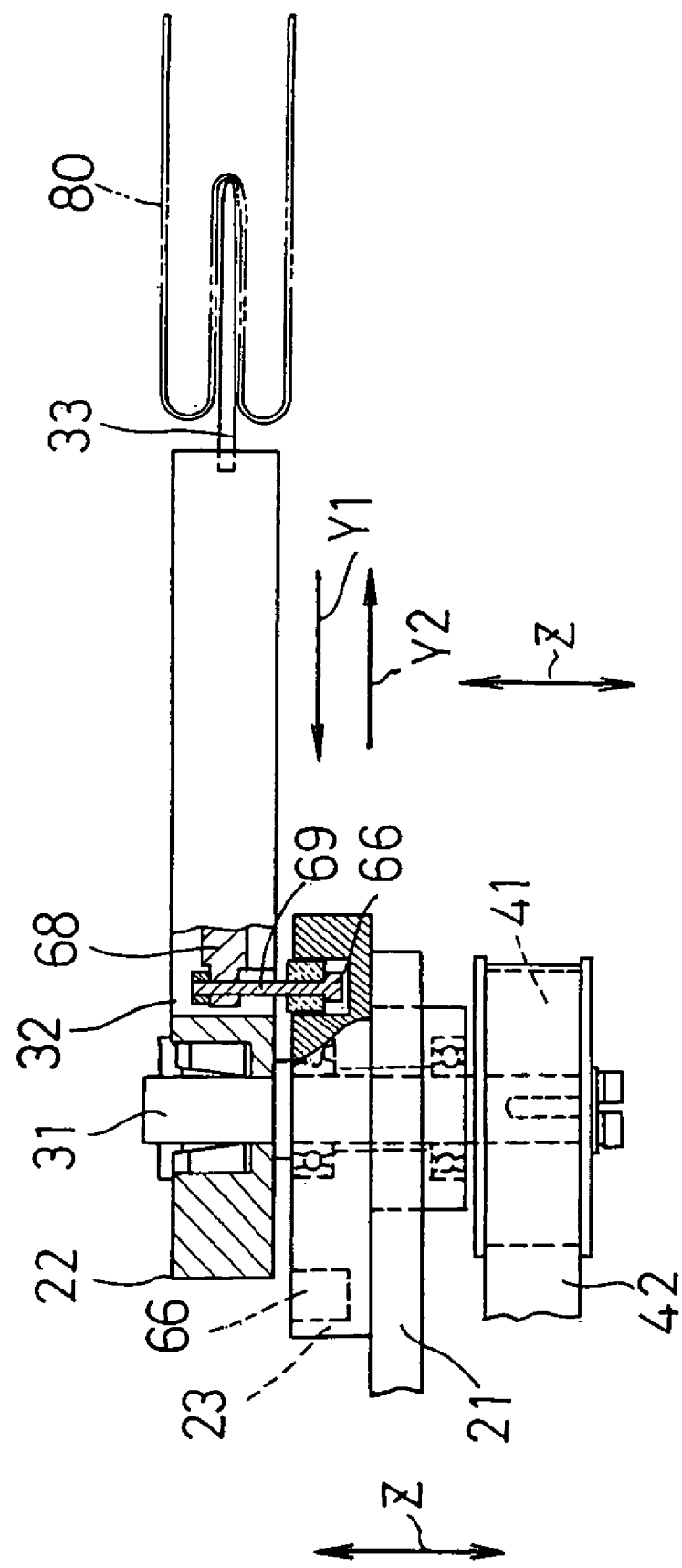
FIG. 12 is a partially cutaway scale-enlarged side view showing a part of FIG. 11.
Figure 13:
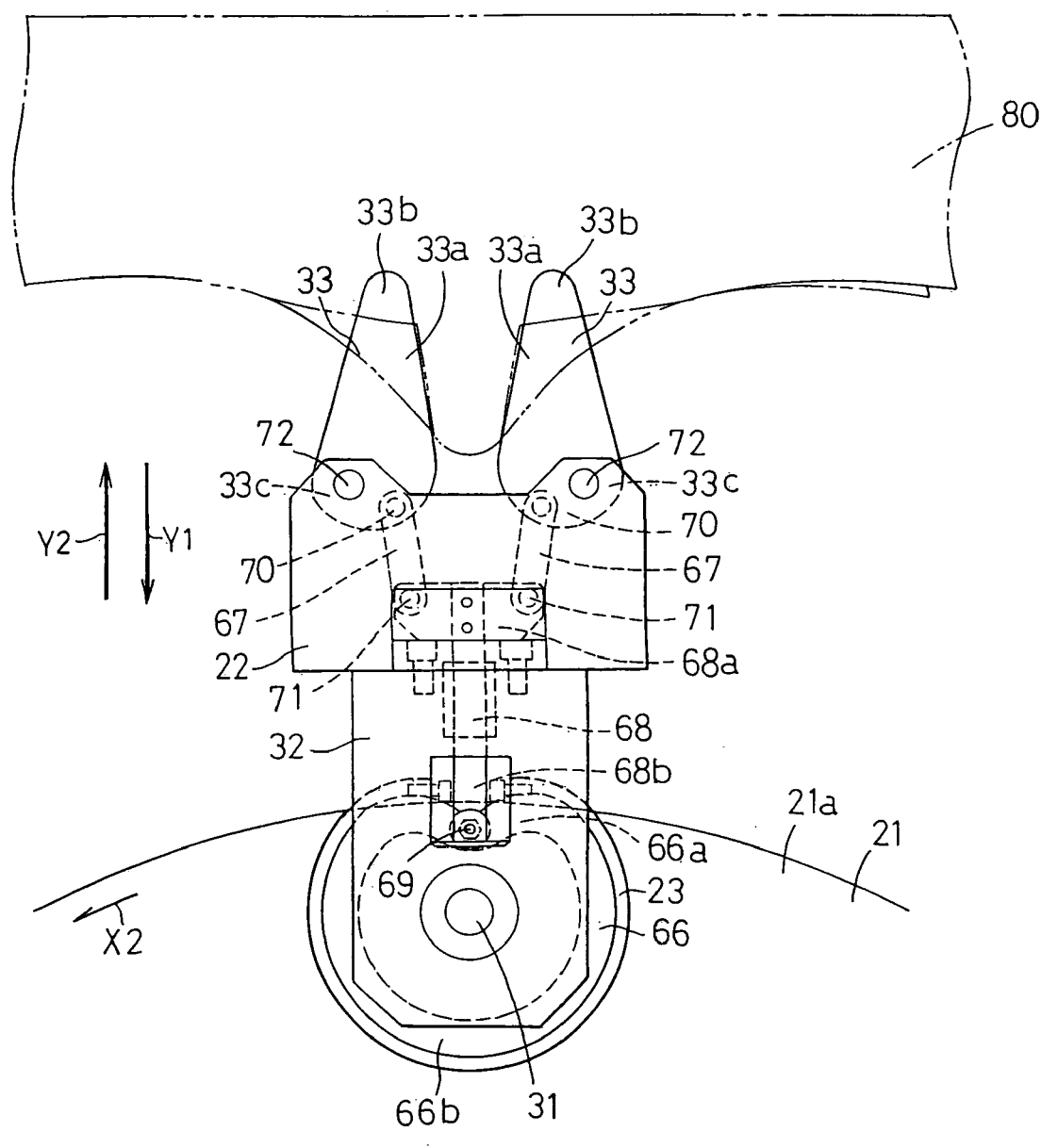
FIG. 13 is a scale-enlarged overhead view of the folding plate.

FIG. 10 is an overhead view showing another example of the apparatus 20, FIG. 11 is a side view corresponding to FIG. 10 showing the apparatus 20, FIG. 12 is a partially cutaway scale-enlarged side view showing a part of FIG. 11 and FIG. 13 is a scale-enlarged overhead view of the folding plate 22. In FIG. 10, the machine direction is indicated by the arrow X and the cross direction is indicated by an arrow Y. In FIGS. 11 and 12, the vertical direction (corresponding to the thickness direction of the contiguous diaper structure 80 folded along the fold 85) is indicated by the arrow Z. In FIG. 12, the guide arms 33 are illustrated as having moved into the inside of the contiguous diaper structure 80. Illustration of the contiguous diaper structure 80 is simplified so that the first web and the second web can not be distinguished from each other and, the core, the waist-circumferential elastic members and the leg-circumferential elastic members are not shown.

The apparatus 20 has a conveyor mechanism (conveyor means) serving to convey the contiguous diaper structure 80 at a constant speed forward in the machine direction indicated by the arrow X1 and a folding mechanism (folding means) serving to fold down the contiguous diaper structure 80 in the crotch regions 82.

The contiguous diaper structure 80 is the same as shown in FIG. 4 and has a plurality of crotch regions 82 (corresponding to the crotch region 6) arranged at regular intervals in the machine direction, a plurality of first waist regions 81 (corresponding to the front waist region 5 or the rear waist region 7) and second waist regions 83 (corresponding to the front waist region 5 or the rear waist region 7) lying on both sides of the respective crotch regions 82 in the cross direction and contiguous to one another, respectively, in the machine direction, and a plurality of leg-holes 84 each formed between each pair of the crotch regions 82 adjacent to each other and arranged at regular intervals in the machine direction.

The conveyor mechanism conveys the contiguous diaper structure 80 forward in the machine direction and, in the course of conveyance, the contiguous diaper structure 80 is in the crotch region 82 folded along the fold 85 extending in the machine direction so that the first and second waist regions 81, 83 may be oppositely spaced apart from each other.

The contiguous diaper structure 80 being conveyed forward in the machine direction is under a predetermined tension exerted thereupon in the machine direction. After the contiguous diaper structure 80 in the crotch region 82 has been folded along the fold 85, such tension acts on the first and second waist regions 81, 83 but substantially does not act on the crotch region 82.

The folding mechanism comprises a first rotary disc 21 lying transversely outside the fold 85 of the contiguous diaper structure 80, six folding plates 22 mounted at regular intervals on the first rotary disc 21 along its peripheral zone 21a and six positive motion cams 23 mounted on the first rotary disc 21 along its peripheral zone 21a so as to be interposed between the first rotary disc 21 and the respective folding plates 22.

The first rotary disc 21 rotates around an axis 24 extending in the direction indicated by an arrow X2 so that the contiguous diaper structure 80 is conveyed forward in the machine direction. Outside the first rotary disc 21, there is provided a gear box 25 adapted to transmit a driving force to the first rotary disc 21. The first rotary disc 21 is provided along its peripheral zone 21a with five guide wheels 26 each lying between each pair of the folding plates 22 adjacent to each other and mounted on the first rotary disc 21 by means of an axis 27 extending in the vertical direction. These guide wheels 26 are rotatable independently of the first rotary disc 21.

An axis 28 of the gear box 25 is rotationally driven by an electric motor (not shown). Within the gear box 25, there is provided a bevel gear (not shown) via which a rotation of the axis 28 is transmitted to an axis 29 extending upward from the gearbox 25 in the vertical direction and an axis 30 extending downward from the gear box 25 in the vertical direction.

Each of the folding plates 22 is mounted on the first rotary disc 21 by means of an axis 31 extending in the vertical direction so as to be rotatable independently of the first rotary disc 21. The folding plates 22 lie outside the fold 85 of the contiguous diaper structure 80 as viewed in the cross direction and arranged at regular intervals along the peripheral zone 21a of the first rotary disc 21. Similarly to these folding plates 22, the positive motion cams 23 are arranged at regular intervals along the peripheral zone 21a of the first rotary disc 21.

The folding plates 22 are adapted to move toward and away from the contiguous diaper structure 80 as the first rotary disc 21 rotates. Each of the folding plates 22 comprises a first base 32 and a pair of guide arms 33 extending from the first base 32 toward the contiguous diaper structure 80 in the cross direction.

The axis 24 of the first rotary disc 21 and the axis 30 of the gearbox 25 are provided with pulleys 34, 35, respectively. These axis 24, 30 are operatively associated with each other by means of open belt 36 guided by the pulleys 34, 35. Rotation of the axis 30 of the gear box 25 is transmitted to the axis 24 of the first rotary disc 21 via the open belt 36. Rotation of the axis 30 causes the first rotary disc 21 to rotate in the same direction indicated by the arrow X2 as the direction in which the axis 24 rotates.

The first rotary disc 21 is provided around its bearing 37 with a pulley 39 adapted to rotate independently of the axis 24. This pulley 39 is rotatably mounted on a bearing 37. The axis 24 is inserted into the bearing 37. The axis 29 of the gear box 25 is provided with a pulley 38. The axis 29 and the pulley 39 are operatively associated with each other via an open belt 40 guided by the pulleys 38, 39. Between the pulley 38 and the pulley 39, there are provided guide wheels 42 serving to keep the belt 40 under tension. The axis 31 of the respective folding plates 22 are provided with pulleys 41. The axis 31 and the pulley 39 are operatively associated with each other via belt 43 guided by the pulleys 39, 41.

More specifically, the belt 43 extends from the pulley 39 to one of the pulleys 41 associated with one of the folding plates 22 and further extends, via the guide wheels 26, to the pulley 41 associated with the adjacent folding plate 22. Rotation of the axis 29 is transmitted via the belt 40 to the pulley 39. Rotation of the pulley 39 is transmitted via the belt 43 to the axis 31 of the folding plates 22. Rotation of the axis 31 causes these folding plates 22 to rotate in a direction indicated by an arrow X3 opposed to the direction indicated by the arrow X2 in which the first rotary disc 21 rotates. In the course of such rotation, the belt 43 is maintained under tension by the guide wheels 26.

A pair of the guide arms 33 are arranged side by side in the machine direction and have respective inner side edges 33a opposed to each other and respective distal ends 33b adapted to swing back and forth in the machine direction. Each of the guide arms 33 is taper down to the distal end 33b. The inner side edges 33a opposed to each other are spaced apart from each other gradually toward the distal ends 33b (See FIG. 8). The guide arms 33 rotate so that respective distal ends 33b may repeatedly down near to and draw away from each other.

In the apparatus 20, the first rotary disc 21 rotates in the direction of the arrow X2 around the axis 24 and the folding plates 22 rotate around the axis 24 of the first rotary disc 21 accordingly. At the same time, each of the folding plates 22 rotates in the peripheral zone 21a of the first rotary disc 21 around the axes 31 thereof in the direction of the arrow X3 opposite to the direction of the arrow X2 in which the first rotary disc 21 rotates. Each of the folding plates 22 rotates by 360° rotation around the axis 31 in the peripheral zone 21a of the first rotary disc 21 while the folding plates 21 rotate by 360° around the axis 24 of the first rotary disc 21 due to rotation of the first rotary disc 21. Consequently, the direction in which the guide arms 33 are opposed to the contiguous diaper structure 80 are always the same. More specifically, in the course of rotation of the folding plates 22 around the axis 24 of the first rotary disc 21, the guide arms 33 always face to the cross direction and there is no possibility that the guide arms 33 might turn to the machine direction.

The positive motion cams 23 are interposed between the first rotary disc 21 and the first bases 32 of the respective folding plates 22 and fixed to the first rotary disc 21. Each of the positive motion cams 23 is formed with an eccentric cam groove 66. The cam groove 66 is defined by a depressed zone 66a sloping down toward the axis 31 of the folding plate 22 and a circular zone 66b extending around a peripheral edge of the positive motion cam 23.

Each of the folding plates 22 has a pair of links 67 mounted on proximal end zones 33c of the guide arms 33, a rod 68 connected to the links 67 and a pin 69 lying in a rear end zone 68b (end zone) of the rod 68 and extending in the vertical direction. The links 67 and the rod 68 extend from the proximal end zones 33c of the guide arms 33 toward the first base 32 in the cross direction. The links 67 are mounted on axes 70 provided in the proximal end zones 33c of the guide arms 33 and on axes 71 lying in a front end zone 68a of the rod 68. The guide arms 33 have the proximal end zones 33c mounted on the first base 32 by means of pivot pins 72. The pin 69 is slidably inserted in the cam groove 66 of the positive motion cam 23.

The positive motion cams 23 rotate around the axis 24 of the first rotary disc 21 due to rotation of the first rotary disc 21 and the pin 69 moves along the cam groove 66 as the first rotary disc 21 rotates. Movement of the pin 69 along the cam groove 66 causes the rod 68 to move back and forth in the cross direction and the guide arms 33 swing back and forth in the machine direction so that the distal ends 33b of the respective guide arms 33 may repeatedly move toward and away from each other accordingly.

The contiguous diaper structure 80 is folded and tucked in the crotch region 82 by the apparatus 20 shown in FIG. 10 in the following manner. The contiguous diaper structure 80 is folded along the fold 85 as the contiguous diaper structure 80 is conveyed forward in the machine direction indicated by the arrow X1 by the conveyor mechanism. The contiguous diaper structure 80 with the first and second waist regions 81, 83 oppositely spaced apart from each other progressively gets nearer to the first rotary disc 21. The first rotary disc 21 is rotating in the direction indicated by the arrow X2 in syncronization with the running speed of the contiguous diaper structure 80.

In the apparatus 20, the guide arms 33 extending from one of the folding plates 22 progressively move into the contiguous diaper structure 80 in the vicinity of a pair of the leg-holes 84 lying on the both sides of the crotch region 82 as the crotch region 82 of the contiguous diaper structure 80 gets nearer to the peripheral zone 21a of the first rotary disc 21.

As the crotch region 82 of the contiguous diaper structure 80 gets nearer to an imaginary line S extending from the axes 24 in the cross direction, the opposite side edges 33a of the guide arms 33 having moved into the contiguous diaper structure 80 come in contact with the crotch region 82 from its outer side and the guide arms 33 swing inward so that the distal ends 33b of the respective guide arms 33 may get close to each other. In this way, the guide arms 33 catch side edge zones 82a of the crotch region 82 extending in the vicinity of the fold 85 between the opposite side edges 33a thereof so as to press these side edge zones 82a into the inside of the contiguous diaper structure 80. Simultaneously, the guide arms 33 move into the clearance 65 defined between the guide blades 54 so that the side edge zones 82a may be held between the guide arms 33 and the guide blades 54 and thereby tucked into the inside of the contiguous diaper structure 80.

In the apparatus 20, the guide arms 33 swing so that the distal ends 33b may be spaced apart from each other as the crotch region 82 of the contiguous diaper structure 80 move away from the peripheral zone 21a of the first rotary disc 21. Thereupon the guide arms 33 progressively retract from the contiguous diaper structure 80. The contiguous diaper structure 80 with the crotch region 82 thus folded and tucked runs away from the first rotary discs 21 in the machine direction.

In the contiguous diaper structure 80 folded in the crotch region 82 along the fold 85, the crotch region 82 is substantially free from affection of the tension exerted upon the first and second waist regions 82, 83, so the side edge zones 82a of the crotch region 82 can be easily tucked and, in addition, the contiguous diaper structure 80 can be conveyed forward in the machine direction with the crotch region 82 reliably kept in a tucked state.

After the side edge zones 82a of the crotch region 82 have been tucked inward, the first and second waist regions 81, 83 oppositely spaced apart from each other now overlap and then the first and second webs are joined by means of two heat-sealing lines 86 extending in the cross direction. These heat-sealing lines 86 are formed so that the individual diaper 1 may have a symmetrical appearance. Subsequently, the first and second webs are cut along cutting lines 87 each extending in the cross direction between two sets of the heat-sealing lines 86 adjacent to each other. These cutting lines 87 extend across the first and second waist regions 81, 83 in the cross direction. The contiguous diaper structure 80 is cut along the respective cutting lines 87 to obtain a plurality of the individual diapers 1 shown in FIG. 1 which are arranged side by side in the machine direction.

This apparatus 20 allows the contiguous diaper structure 80 in the crotch region 82 to be continuously and rapidly folded and tucked inward. Furthermore, the apparatus 20 allows the side edge zone 82a of the crotch region 82 to be reliably folded and tucked inward since the guide arms 33 catch the side edge zones 82a to press these side edge zones 82a into the inside of the contiguous diaper structure 80.

While the positive motion cams 23 are used in the illustrated embodiments of the apparatus 20 according to this invention for the purpose of swinging the guide arms 33 so that the distal ends 33b thereof may get nearer to and draw away from each other, it is possible to adopt solenoids for the same purpose. In this case, moving iron cores of the respective solenoids may move away from each other to swing the guide arms 33 in the direction in which the distal ends 33b thereof get nearer to each other and the moving iron cores of the respective solenoids may come in contact with each other to swing the guide arms 33 in the direction in which the guide arms 33 move away from each other.

A stock material for the liquid-pervious continuous first web (corresponding to the liquid-pervious topsheet 2) may be selected from the group consisting of a hydrophilic fibrous nonwoven fabric, a hydrophobic fibrous nonwoven fabric having a plurality of perforations and a finely perforated plastic film. A stock material for the liquid-impervious continuous second web (corresponding to the liquid-impervious backsheet 3) may be selected from the group consisting of a hydrophobic fibrous nonwoven fabric, a breathable but liquid-impervious plastic film, a composite nonwoven fabric comprising two or more layers of hydrophobic fibrous nonwoven fabric placed upon one another and a composite sheet comprising a hydrophobic fibrous nonwoven fabric and a breathable but liquid-impervious plastic film laminated upon each other.

A nonwoven fabric may be selected from the group consisting of those obtained by spun lace-, needle punch-, melt blown-, thermal bond-, spun bond-, chemical bond- and air-through-processes. A component fiber of nonwoven fabric may be selected from the group consisting of polyolefine-, polyester- and polyamide-based fibers, core-and-sheath type conjugated fiber and side-by-side type conjugated fiber of polyethylene/polypropylene and polyethylene/polyester.

The core 4 is a mixture of fluff pulp and super-absorbent polymer particles or a mixture of fluff pulp, super-absorbent polymer particles and thermoplastic synthetic resin fibers compressed to a desired thickness. Preferably, the core 4 is entirely covered with a liquid-pervious sheet such as tissue paper or hydrophilic nonwoven fabric in order to prevent the core 4 from getting out of shape and/or to prevent falling off of the polymer particles. Polymer particles may be selected from the group consisting of starch-based, cellulose-based and synthetic polymer-based particles.

The apparatus and the method for folding and tucking disposable diapers in their crotch regions has advantageous effects that the contiguous diaper structure running in the machine direction can be folded and tucked into the inside of the contiguous diaper structure. The apparatus provided along the peripheral zone of the first rotary disc with a plurality of the folding plates allows the crotch regions of the contiguous diaper structure to be continuously and rapidly folded and tucked inward.

With the apparatus in which the guide arms of the respective folding plates swing back and forth in the machine direction, the guide arms catch the opposite side edge zones of the crotch region to press these side edge zones into the inside of the contiguous diaper structure and thereby to ensure that the crotch region can be reliably tucked inward.

With the apparatus comprising, in addition to the folding plates, the auxiliary plates, the guide arms move into the clearance between the guide blades of the auxiliary plate as the guide arms of the folding plate swing so that the side edge zones of the crotch region may be held between the guide arms and the guide blades. In this way, the crotch region can be further reliably tucked inward.

The individual diaper having its crotch region folded and tucked by the apparatus according to this invention might not create a discomfortable feeling against the wearer because the crotch region is properly received by the wearer's crotch region as the diaper is put on the wearer's body. Furthermore, even if the crotch region is squeezed by the wearer's crotch, it is not likely that the crotch region might be irregularly folded and/or the core might be formed with a plurality of irregular creases. In this way, there is no anxiety that the bodily discharge absorbing capacity in the crotch region might be deteriorated.

This diaper is free from the inconvenience that the wearer's toes and/or heels might get stuck on the side edge zones of the crotch region as the wearer's legs are guided through the waist-hole and then through the leg-holes to put the diaper on the wearer's body. In this way, the diaper can be smoothly put on the wearer's body.

What is claimed is:

1. An apparatus for folding and tucking a contiguous diaper structure running in a machine direction, said contiguous diaper structure including a plurality of crotch regions arranged at regular intervals in said machine direction and a plurality of first and second waist regions lying both sides of said crotch regions in a cross direction orthogonal to said machine direction and having a plurality of leg-holes each formed between each pair of said crotch regions adjacent to each other, said apparatus comprising:

a conveyor mechanism folding said contiguous diaper structure along a fold in said crotch region so that said first and second waist regions are oppositely spaced apart from each other and conveying said contiguous diaper structure in said machine direction with said contiguous diaper structure kept folded;

a folding mechanism tucking said crotch region of said contiguous diaper structure into the inside of said contiguous diaper structure from said leg-holes lying on both sides of said crotch region;

said folding mechanism including folding plates adapted to move toward and away from said crotch region of said contiguous diaper structure in said cross direction in syncronization with running of said contiguous diaper structure in said machine direction;

each of said folding plates comprising a first base and a pair of guide arms extending from said first base in said cross direction and aligned in said machine direction; and said guide arms moving into the inside of said contiguous diaper structure as said folding plate moves toward said crotch region of said contiguous diaper structure in order to catch opposite side edges of said crotch region in the vicinity of said fold from the outer side.

2. The apparatus according to claim 1, wherein each of said guide arms has a proximal end and a distal end, said proximal end is fixed to said first base and said distal end repeatedly swing back and forth so that said opposite side edges of said guide arms get near to each other as said guide arms move into said contiguous diaper structure and get away from each other as said guide arms retract from said contiguous diaper structure.

3. The apparatus according to claim 1, wherein said folding mechanism includes a first rotary disc adapted to rotate around an axis extending in a vertical direction, a plurality of said folding plates are arranged in a peripheral zone of said first rotary disc at regular intervals and mounted thereon by means of an axis extending in said vertical direction so as to rotate around said axis, said folding plates rotate around said axis of said first rotary disc as said first rotary disc rotates around its own axis and each of said folding plates rotates around its own axis by 360° while said first rotary disc rotates around its own axis by 360° so that a direction to which said guide arms are opposed is always the same during rotation of said folding plates and said pair of said guide arms moves in said cross direction into said contiguous diaper structure to catch and press said crotch region of said contiguous diaper structure as said crotch region of said contiguous diaper structure gets nearer to said peripheral zone of said first rotary disc and moves in said cross direction apart from said contiguous diaper structure as said contiguous diaper structure gets away from said peripheral zone of said first rotary disc.

4. The apparatus according to claim 3, wherein said folding mechanism includes a plurality of positive motion cams arranged in said peripheral zone of said first rotary disc at regular intervals and fixed thereon, each of said folding plates comprises links mounted on said proximal ends of said guide arms, a rod connected to said guide arms by means of said link and extending in said cross direction and a pin extending through an end zone of said rod and said first base in said vertical direction, said pin is slidably inserted into an eccentric cam groove of said positive motion cam and each of said positive motion cams rotates around said axis of said first rotary disc due to rotation of said first rotary disc and said pin moves along said cam groove so that said rod moves back and forth in said cross direction and said guide arms swing back and forth in said machine direction by means of said links and thereby said distal ends of said guide arms repeatedly get near to and away from each other.

5. The apparatus according to claim 1, wherein said folding mechanism includes a plurality of auxiliary plates located so as to be opposed to said folding plates and adapted to move toward and away from said crotch region of said contiguous diaper structure between said first and second waist regions oppositely spaced apart from each other in synchronization with running of said contiguous diaper structure in said machine direction, each of said auxiliary plates comprises a second base and a pair of guide blades arranged side by side in said vertical direction and extending from said second base in said cross direction, each of said guide blades has a distal end tapered toward said cross direction, said guide arms and said guide blades synchronously move into said contiguous diaper structure and simultaneously said guide arms move into a clearance defined between said pair of said guide blades so that said crotch region is held between said guide arms and said guide blades and thereby tucked into the inside of said contiguous diaper structure.

6. The apparatus according to claim 5, wherein said folding mechanism includes a second rotary disc located so as to be opposed to said first rotary disc and adapted to rotate around an axis extending in said vertical direction, a plurality of said auxiliary plates are arranged in a peripheral zone of said second rotary disc at regular intervals and mounted thereon by means of an axis extending through said second base in said vertical direction so as to rotate around said axis, said auxiliary plates rotate around said axis of said second rotary disc as said second rotary disc rotates around its own axis and each of said auxiliary plates rotates around its own axis by 360° while said second rotary disc rotates around its own axis by 360° so that a direction to which said guide blades are opposed is always the same during rotation of said auxiliary plate and each of said guide blades moves in said cross direction into said contiguous diaper structure between said first and second waist regions as said crotch region of said contiguous diaper structure gets nearer to said first and second rotary discs and moves in said cross direction apart from said contiguous diaper structure as said contiguous diaper structure gets away from said first and second rotary discs.

7. The apparatus according to claim 1, wherein said contiguous diaper structure comprises a liquid-pervious continuous first web, a liquid-impervious continuous second web and a plurality of liquid-absorbent cores each interposed between said first and second webs and extending from said crotch region toward said first and second waist region in said cross direction.

* * * * *